(12) United States Patent
Hsu et al.

(10) Patent No.: US 11,370,929 B2
(45) Date of Patent: Jun. 28, 2022

(54) BIOINK SET AND APPLICATIONS THEREOF FOR THREE-DIMENSIONAL PRINTING OF CELLS

(71) Applicant: National Taiwan University, Taipei (TW)

(72) Inventors: Shan-hui Hsu, Taipei (TW); Cheng-Tien Hsieh, Taipei (TW)

(73) Assignee: NATIONAL TAIWAN UNIVERSITY, Taipei (TW)

(*) Notice: Subject to any disclaimer, the term of this patent is extended or adjusted under 35 U.S.C. 154(b) by 245 days.

(21) Appl. No.: 16/055,676

(22) Filed: Aug. 6, 2018

(65) Prior Publication Data

US 2019/0225824 A1 Jul. 25, 2019

(30) Foreign Application Priority Data

Jan. 25, 2018 (TW) ................................ 107102761

(51) Int. Cl.

| | | |
|---|---|---|
| *C09D 11/102* | (2014.01) | |
| *C09D 11/04* | (2006.01) | |
| *C09D 11/14* | (2006.01) | |
| *A61L 27/26* | (2006.01) | |
| *A61L 27/38* | (2006.01) | |
| *B33Y 10/00* | (2015.01) | |
| *B33Y 70/00* | (2020.01) | |
| *B29C 64/106* | (2017.01) | |
| *B29C 64/209* | (2017.01) | |
| *B33Y 30/00* | (2015.01) | |
| *A61L 27/58* | (2006.01) | |
| *B33Y 80/00* | (2015.01) | |
| *B29K 75/00* | (2006.01) | |
| *B29K 105/00* | (2006.01) | |

(52) U.S. Cl.
CPC ............ *C09D 11/102* (2013.01); *A61L 27/26* (2013.01); *A61L 27/38* (2013.01); *A61L 27/58* (2013.01); *B33Y 70/00* (2014.12); *C09D 11/04* (2013.01); *C09D 11/14* (2013.01); *B29K 2075/00* (2013.01); *B29K 2105/0061* (2013.01); *B29K 2995/006* (2013.01); *B33Y 80/00* (2014.12)

(58) Field of Classification Search
CPC .......... A61L 27/26; A61L 27/58; A61L 27/52; A61L 27/38; C08L 5/04; C08L 5/08; C08L 5/12; C08L 75/04; C08L 89/06; B29K 2075/00; B29K 2105/0061; B29K 2995/006; B29C 64/106; B33Y 70/00; B33Y 80/00; C09D 11/04; C09D 11/102; C09D 11/108; C09D 11/14

See application file for complete search history.

(56) References Cited

U.S. PATENT DOCUMENTS

| | | | |
|---|---|---|---|
| 2012/0029654 A1* | 2/2012 | Xu ............................ | B32B 5/26 623/23.72 |
| 2012/0183622 A1* | 7/2012 | Guelcher ............. | A61K 9/5036 424/497 |
| 2017/0218228 A1* | 8/2017 | Jose ........................ | B33Y 80/00 |

FOREIGN PATENT DOCUMENTS

| | | | | |
|---|---|---|---|---|
| WO | WO 2016/161944 | * | 10/2016 | ............. A61L 27/44 |
| WO | WO 2017/014582 | * | 1/2017 | ............. A61L 27/54 |

OTHER PUBLICATIONS

Lee et al. (Progress in Organic Coatings 77(2014) 1111-1116) (Year: 2014).*
Of Lin et al. (Journal of Materials Chemistry B, 2016, 4, 6694). (Year: 2016).*
Lin Ho et al., "Cell reprogramming by 3D bioprinting of human fibroblasts in polyurethane hydrogel for fabrication of neural-like constructs", Acta Biomaterialia 70 (2018) 57-70.
Yu-Jen Wang et al., "Biodegradable Water-Based Polyurethane Shape Memory Elastomers for Bone Tissue Engineering", ACS Biomater. Sci. Eng., 2018, 4 (4), pp. 1397-1406.
Gu et al. "Advanced Bioink for 3D Bioprinting of Complex Free-Standing Structures with High Sliffness", Nov. 7, 2020, Bioengineering, www.mdpi.com/journal/bioengineering.

* cited by examiner

*Primary Examiner* — Anna R Falkowitz
(74) *Attorney, Agent, or Firm* — WPAT, PC

(57) ABSTRACT

Provided is a bioink set for printing a construct that is able to carry cells, including a bioink which contains a biodegradable polyurethane and a biopolymer, and a divalent metal ion solution. The biopolymer is gelatin, agar, alginate salts, hyaluronic acid and salts thereof, chitosan, and any combination thereof. Also provided are a method of preparing a construct for carrying cells by three-dimensional printing with the bioink set, and a method of three-dimensional printing of cells by using an ink composition.

4 Claims, 24 Drawing Sheets

Specification includes a Sequence Listing.

BIOINK SET AND APPLICATIONS THEREOF FOR THREE-DIMENSIONAL PRINTING OF CELLS

CROSS-REFERENCE TO RELATED APPLICATION

This application claims priority of Taiwan patent application No. 107102761, filed on Jan. 25, 2018, the content of which is incorporated herein in its entirety by reference.

BACKGROUND OF THE INVENTION

1. Field of the Invention

The present invention relates to ink materials and methods for three-dimensional bioprinting. Particularly, the present invention relates to a bioink set, a method of preparing cell-loaded constructs by performing three-dimensional printing using the bioink set, and a method of performing three-dimensional printing of cells using an ink composition.

2. The Prior Art

Three-dimensional (3D) bioprinting is an emerging technology that combines tissue engineering with 3D printing. It may be utilized to produce a variety of artificial constructs that have predetermined structures and perform specific functions, thereby repairing or reconstructing human tissues and organs. Conventional polymeric materials for 3D printing need to be melted at high temperatures or dissolved in organic solvents to obtain fluidity and printability before being hardened to form solid structures by subsequent photo-crosslinking or changes in temperature, ion concentration, and pH value. The processes requiring high temperatures or toxic solvents have made these polymeric materials unsuitable for direct printing with living cells.

Alternatively, water-soluble polymers which may be crosslinked by light irradiation or gelled in response to changes in temperature, ion, or pH are more suitable as bioink materials for direct printing of living cells. For example, photocrosslinkable inks typically include an initiator that generates free radicals upon ultraviolet irradiation to initiate a crosslinking reaction, thereby forming a printed product with high pattern fidelity and good mechanical properties. However, such initiator is cytotoxic and the step of ultraviolet irradiation damages the cells.

Temperature-sensitive inks are less harmful to cells, but the stacked structures formed therefrom have limited integrity and strength due to the slow temperature-induced phase transition. In addition, temperature-sensitive inks once subjected to preheating cannot be used for long-term printing because of the specific and limited duration of phase transition.

Ion-sensitive inks such as those containing sodium alginate are generally hardened with an ionic solution. The resulting gels have high water content and are suitable for living cells, but their mechanical properties are poor. pH-sensitive inks are mostly made of collagen, which is easy to print, but the printed products are often lack of strength.

Bioinks are generally categorized into synthetic and natural materials depending on the source. Synthetic materials include polyethylene glycol (PEG), polycaprolactone (PCL), polylactide (PLA), polyurethane (PU), polyethylene glycol dimethacrylates (PEGDMA), and Pluronic. These materials have the advantages of ease to obtain, better stability and mechanical properties, and tunable degradation rates. Nevertheless, they have lower cell compatibility and their degradation products often have adverse effects on cells.

Natural materials include collagen, fibrin, sodium alginate, and gelatin. These materials are usually derived from extracellular matrix, and therefore the materials and their degradation products often have neutral or positive effects on cells. However, their mechanical properties are generally poor. For example, gelatin is a fluid at 37° C. and requires treatment with crosslinking agents such as glutaraldehyde and 1-ethyl-3-(3-dimethylaminopropyl)carbodiimide (EDC, also termed 3-ethyliminomethyleneamino-N,N-dimethyl-propan-1-amine) to maintain the colloidal state at 37° C. However, the crosslinking agents are toxic, and therefore it has been reported that the mixture of gelatin and polyurethane treated with the crosslinking agents cannot be used as a bioink for printing living cells.

The main challenge in development of 3D bioprinting at the current stage is to allow the printed products to have appropriate mechanical strength, high cell compatibility, and high pattern fidelity. Therefore, it is of necessity to develop new bioink materials and new methods for 3D bioprinting in order to produce artificial constructs possessing the aforementioned characteristics.

SUMMARY OF THE INVENTION

As a result, the present invention provides a bioink set for printing a construct that is able to carry cells. The bioink set includes a bioink and a divalent metal ion solution, wherein the bioink includes a biodegradable polyurethane and a biopolymer selected from the group consisting of gelatin, agar, and alginate salts, hyaluronic acid and salts thereof, chitosan, and any combinations thereof.

In one embodiment of the present invention, the divalent metal ion solution includes a divalent alkaline earth metal ion. The biodegradable polyurethane includes a hard segment conjugated to a soft segment, the hard segment is formed by reacting diisocyanate with a chain extender, the soft segment is at least an oligomer diol, and the chain extender includes an anionic chain extender. The biodegradable polyurethane and the biopolymer are at a weight ratio ranging from 85:15 to 5:95.

In another aspect, the present invention provides a method of printing a construct for carrying cells, including in sequence the following steps: (a) extruding a bioink to build a gel object having a predetermined structure, wherein the bioink includes a biodegradable polyurethane and a biopolymer selected from the group consisting of gelatin, agar, alginate salts, hyaluronic acid and salts thereof, chitosan, and any combinations thereof; and (b) contacting the gel object with a divalent metal ion solution for a predetermined period of time to obtain a construct having the predetermined structure.

In one embodiment of the present invention, the bioink in the step (a) further includes a cell; the bioink is at a temperature from 20° C. to 35° C. and is extruded through a syringe including a nozzle having a diameter of at least 50 μm. In the step (b), the divalent metal ion solution includes a divalent alkaline earth metal ion and the predetermined period of time is from 5 to 60 minutes.

In still another aspect, the present invention provides a method of three-dimensional printing of cells, including the step of using an ink composition including a biodegradable polyurethane and a biopolymer selected from the group consisting of gelatin, agar, alginate salts, hyaluronic acid and salts thereof, chitosan, and any combinations thereof.

The bioink material of the present invention has high biocompatibility and specific rheological properties and thus is suitable for high-resolution, high-fidelity, and long-term 3D bioprinting. Moreover, the printing method of the present invention effectively enhances the mechanical properties and structural stability of printed products by the interactions between polyurethanes, biopolymers, and divalent metal ions without impairing cell viability. Due to these characteristics, the bioink and printing method of the present invention can be used to produce artificial tissues or scaffolds for living organisms, or to produce in vitro drug screening platforms.

The present invention is further described in the following examples, in reference to the accompanying drawings. It should be understood that the examples given below do not limit the scope of the invention, and that modifications can be made without departing from the scope of the appended claims.

DETAILED DESCRIPTION OF THE PREFERRED EMBODIMENT

Figure 1A:
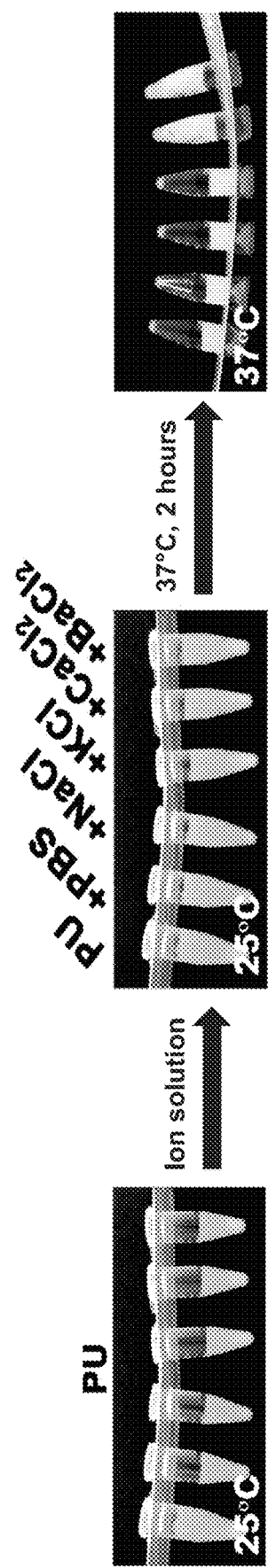
FIG. 1A shows the change in appearance at 25° C. and 37° C. after mixing polyurethane (PU) dispersion with different metal ion solutions, including a sodium chloride (NaCl) solution, a potassium chloride (KCl) solution, a calcium chloride ($CaCl_2$) solution, a barium chloride ($BaCl_2$) solution, and phosphate buffered saline (PBS)

The present invention provides a bioink set for printing a construct that is able to carry cells and a method of printing a construct for carrying cells by using the bioink set to perform 3D printing. The bioink set includes a bioink that can be printed with cells and a divalent metal ion solution that enhances the structural stability of the initial printed products. The bioink includes a biodegradable polyurethane and a biopolymer selected from the group consisting of gelatin, agar, alginate salts, hyaluronic acid and salts thereof, chitosan, and any combinations thereof; and the divalent metal ion solution preferably includes a divalent alkaline earth metal ion. When the bioink set is used to print a construct for carrying cells, the first step is to extrude the bioink to build a gel object having a predetermined structure through layer-by-layer stacking, and the following step is to contact the gel object with the divalent metal ion solution for a predetermined period of time to obtain a construct having that predetermined structure. The following examples illustrate the preparation of the bioink of the present invention and the characteristics thereof, including biocompatibility, rheological properties, and mechanical properties after gelation. The examples also illustrate in detail the steps of the printing method of the present invention, and demonstrate the viability and differentiation of cells in the construct.

Definition

Numerical quantities provided herein are approximated, experimental values that may vary within 20 percent, preferably within 10 percent, and most preferably within 5 percent. Thus, the terms "about" and "approximately" refer to within 20 percent, preferably within 10 percent, and most preferably within 5 percent of a given value or range.

The expression "a predetermined period of time" used herein refers to a period of time that is required to contact a gel object having a predetermined structure with a divalent metal ion solution to obtain a construct having and maintaining the predetermined structure.

Materials and Methods
Synthesis of Biodegradable Polyurethane

In all the examples herein, the biodegradable polyurethane (also referred to as polyurethane) is temperature-sensitive polyurethane synthesized by a water-based process. The biodegradable polyurethane has a main chain which includes a hard segment conjugated to a soft segment. The hard segment is formed by reacting diisocyanate with a chain extender. The diisocyanate may be isophorone diisocyanate (IPDI). The chain extender includes an anionic chain extender and a second chain extender. One example of the anionic chain extender is 2,2-bis(hydroxymethyl)propionic acid (DMPA); and one example of the second chain extender is ethylenediamine (EDA) which is short-chain and highly reactive. The soft segment is at least one oligomer diol, such as poly(ε-caprolactone) diol (PCL diol), poly(D, L-lactide) diol (PDLA diol), poly(L,L-lactide) diol (PLLA diol), poly(3-hydroxybutyrate) diol (PHB diol), polyethylene butylene adipate diol (PEBA diol), or combinations thereof. The properties of biodegradable polyurethane may be adjusted by changing the constituents of the hard segment and the soft segment.

In one embodiment, the biodegradable polyurethane contains 62 wt % soft segments and is formed by reaction of oligomer diol, IPDI, DMPA, and EDA in a stoichiometric ratio of 1:3.52:1:1.52. The synthetic process of this biodegradable polyurethane is briefly described below. PCL diol (molecular weight of about 2 g/mol; Sigma) and PDLA diol (molecular weight of about 2 g/mol) were added to a four neck vessel at a molar ratio of 4:1 and mixed with stirring (180 rpm) under nitrogen atmosphere for 30 min at 95° C., followed by reaction with tin(II) 2-ethylhexanoate (T-9; Alfa Aesar), used as a catalyst, and IPDI (Evonik Degussa GmbH) for 3 hours. Subsequently, DMPA (Sigma) and methyl ethyl ketone (MEK; J. T. Baker), used as a solvent, were added to the four neck vessel for reaction at 75° C. for 1 hour with stirring, and then triethylamine (TEA; R.D.H.) was added to the vessel for neutralization after the temperature was decreased to 50° C. The resulting reaction mixture was dispersed in deionized water by stirring at 1100 rpm, and EDA (Tedia) was added to obtain a biodegradable polyurethane dispersion (with solid content of about 30 wt %). The residual solvent in the dispersion was removed by vacuum distillation. This temperature-sensitive biodegradable polyurethane material forms a solid hydrogel at 37° C., and thus it needs to be pre-heated when used alone in 3D printing. Moreover, in the case where the solid content is less than 20 wt %, the heated polyurethane is unable to form a multi-layer stack structure due to its insufficient mechanical properties.

Cell Culture

Human derived pluripotent stem cell-derived mesenchymal stem cells (referred to as hiPS-MSCs) were prepared as follows. First, a lentivirus (Sigma) carrying a gene of octamer-binding transcription factor 4 (Oct4) and a gene of sex determining region Y (SRY)-box 2 (Sox2) was used to transfect human umbilical vein endothelial cells (BCRC H-UV001) to obtain human induced pluripotent stem cells (hiPS cells), which were cultured in human embryonic stem (hES) cell medium (ReproCELL) containing 4 ng/mL human basic fibroblast growth factor at 37° C. under 5% $CO_2$. The hiPS cells were differentiated into mesenchymal stem cells, namely hiPS-MSCs, once cultured in a mesenchymal stem cell culture medium (Gibco) for 6 days. The hiPS-MSCs were cultured in a basal medium, that is, the DMEM-LG medium (Dulbecco's modified Eagle's medium-Low glucose; Gibco) supplemented with 3.7 g/L sodium bicarbonate (Sigma), 1% penicillin-streptavidin (Gibco), 1% L-glutamine (Gibco), and 10% fetal bovine serum (FBS; Caisson Laboratories). The hiPS-MSCs were incubated at 37° C. in 5% $CO_2$ with the medium being refreshed twice a week.

Rheological Measurement

Polyurethane/gelatin hydrogel was loaded on a rheometer (HR2; TA Instruments) with a cone geometry. The cone has a diameter of 40 mm and an angle of 2°. The measurement was performed in either dynamic or static mode. In dynamic mode, the gelation temperature of the hydrogel was determined by oscillation temperature sweep at a strain of 1% and a frequency of 1 Hz. In addition, oscillation strain sweep was performed at a strain range of 0.01-2500% and a frequency of 1 Hz at 25° C., and oscillation frequency sweep was performed at a strain of 1% and a frequency range of 0.1-100 Hz at 25° C. In static mode, the steady shear viscosity of the hydrogel at 25° C. was measured at a shear rate range of 0.1-3000 $s^{-1}$.

Measurement of Mechanical Properties

The polyurethane/gelatin hydrogel was allowed to sit at 25° C. or 37° C. for 3 minutes before measurement of compression properties at a static rate of 3% strain/min or measurement of tensile properties at a static rate of 0.2 N/min using a dynamic mechanical analyzer (DMA) (Q-800; TA Instruments).

Differentiation of hiPS-MSCs

To obtain chondro-differentiated hiPS-MSCs, the construct carrying hiPS-MSCs was incubated in the basal medium for 24 hours and then incubated with a chondrogenic induction medium for seven days at 37° C. The chondrogenic induction medium contained the basal medium, 10 ng/mL transforming growth factor-β3 (TGF-β3; CytoLab/Peprotech, Israel), 0.1 µM dexamethasone (Sigma), 40 µg/mL L-proline (Sigma), 50 µg/mL ascorbate-2-phosphate (Sigma), and 1% insulin-transferrin-selenium (ITS)-premix 100× (Sigma).

Gene Expression Analysis

Quantitative polymerase chain reaction (qPCR) technique was used to determine gene expression of proteins including sex determining region Y-box 9 (SRY-box 9, Sox9), aggrecan (Agg), type I collagen (Col I), type II collagen (Col II), and type X collagen (Col X). In brief, according to the manufacturer's instructions, total RNA was isolated from cells using Trizol reagent (Invitrogen) and then reverse transcribed into complementary DNA (cDNA) at 37° C. with RevertAid First Strand cDNA Synthesis Kit (MBI Ferments, Germany) Thereafter, qPCR was conducted in a PCR thermocycler (StepOnePlus thermo cycler; Applied Biosystems) using a qPCR commercial kit (DyNAmo Flash SYBR Green; FinnzymesOy, Finland) and primers for Agg, Sox9, Col I, Col II, Col X, and glyceraldehyde 3-phosphate dehydrogenase (GAPDH). The gene expression level of each gene was normalized to that of GAPDH. The nucleotide sequences of primers are listed in TABLE 1.

TABLE 1

| Gene | The sequences of forward (F) and reverse (R) primers | Annealing temperature (° C.) |
|---|---|---|
| Sox9 | F: TTGAGCCTTAAAACGGTGCT (SEQ ID NO: 1)<br>R: CTGGTGTTCTGAGAGGCACA (SEQ ID NO: 2) | 62 |
| Agg | F: ACAGCTGGGGACATTAGTGG (SEQ ID NO: 3)<br>R: GTGGAATGCAGAGGTGGTTT (SEQ ID NO: 4) | 62 |
| Col I | F: GAAGAGTGGAGAGTACTGGATTGAC (SEQ ID NO: 5)<br>R: GGTTCTTGCTGATGTACCAGTTC (SEQ ID NO: 6) | 58 |
| Col II | F: TCACGTACACTGCCCTGAAG (SEQ ID NO: 7)<br>R: TGCAACGGATTGTGTTGTTT (SEQ ID NO: 8) | 58 |
| Col X | F: TCACCAAAGAAGTCCTGCTA (SEQ ID NO: 9)<br>R: GATACCTCCTGGATGTTTCCTA (SEQ ID NO: 10) | 62 |
| GAPDH | F: TCACTGCCACCCAGAAGACT (SEQ ID NO: 11)<br>R: TTCTAGACGGCAGGTCAGGT (SEQ ID NO: 12) | 62 |

Statistical Analysis

All of the experimental data are expressed as mean±standard deviation (S.D.). Each experiment was independently repeated three times to verify reproducibility. Statistical differences between experimental groups were determined by analysis of variance and Student's T test. Groups with a p-value less than 0.05 are considered to be statistically significant different and marked with the symbol *.

Example 1

Preparation of the Bioink

For preparation of the bioink of the present invention, a biodegradable polyurethane dispersion is mixed well aqueous solution of biopolymers selected from the group consisting of gelatin, agar, alginate salts, hyaluronic acid and salts thereof, chitosan, and any combinations thereof to form a polyurethane/biopolymer hydrogel, for example, a polyurethane/gelatin hydrogel. The weight ratio of the biodegradable polyurethane to the biopolymer ranges from 85:15 to 5:95. Unless otherwise specified, the bioink described in the following examples includes a hydrogel prepared by mixing 12.5% (w/v) biodegradable polyurethane dispersion and 12.5% (w/v) gelatin (Sigma) aqueous solution at a solid content ratio of 80:20. One example of the biodegradable polyurethane is formed by reaction of oligomer diol, IPDI, DMPA, and EDA in a stoichiometric ratio of 1:3.52:1:1.52 and is designated as PU in Example 2.1.

In order to provide an environment that promotes the survival of specific type of cells prior to cell printing, the bioink may be modified by addition of salts such as sodium bicarbonate, cell culture medium such as DMEM-LG medium, or other substances such as antibiotics and cell differentiation inducers. The addition allows the polyurethane/gelatin hydrogel to have the same ionic strength as the cell culture medium.

Example 2

Gelation Test on the Bioink 2.1 Effects of Metal Ions on the Gelation of Bioink Components The effects of different metal ions on the gelation of each component of the bioink were investigated. 12.5% (w/v) PU dispersion or 12.5% (w/v) gelatin aqueous solution was mixed at equal volume with a 0.2 N aqueous solution of potassium chloride (KCl), sodium chloride (NaCl), calcium chloride ($CaCl_2$), or barium chloride ($BaCl_2$) or phosphate buffered saline (PBS), and the resulting mixtures were examined for the change in appearance after allowed to sit at 25° C. for 5 minutes and then transferred to a 37° C. incubator for 2 hours.

Figure 1B:
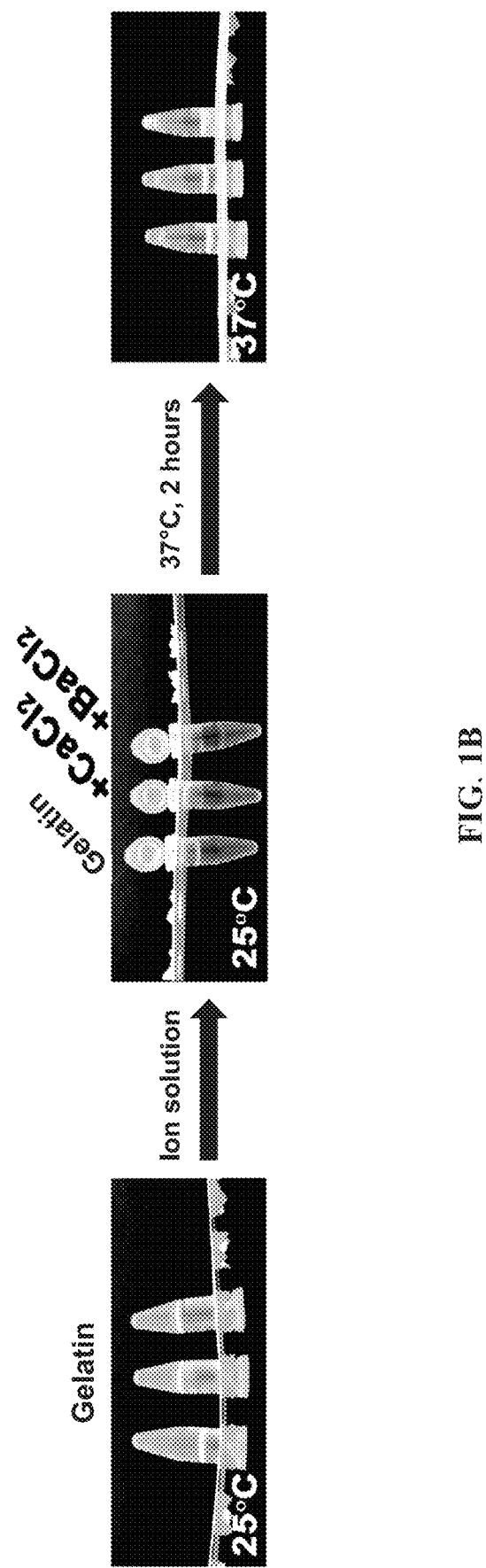
FIG. 1B shows the change in appearance at 25° C. and 37° C. after mixing a gelatin aqueous solution with different metal ion solutions, including a calcium chloride solution and a barium chloride solution.

FIG. 1A shows the change in appearance at 25° C. and 37° C. after mixing polyurethane (PU) dispersion with different metal ion solutions; FIG. 1B shows the change in appearance at 25° C. and 37° C. after mixing a gelatin aqueous solution with different metal ion solutions. According to FIG. 1A, treatment with PBS, sodium chloride, or potassium chloride at 25° C. did not significantly alter the liquid appearance of the polyurethane dispersion, but partial gelation was observed in the group treated with calcium chloride or barium chloride. At 37° C., the group treated with PBS, sodium chloride, or potassium chloride was still in liquid form, while the group treated with calcium chloride or barium chloride remained in gel form. According to FIG. 1B, the gelatin aqueous solution without any treatment was gel-like at 25° C. but liquid at 37° C. In contrast, the gelatin aqueous solution treated with calcium chloride or barium chloride appeared as a liquid at 25° C. and 37° C. The results show that treatment with divalent alkaline earth metal ions such as calcium and barium ions enhances the gel formation ability of biodegradable polyurethane, but such treatment is unfavorable to or ineffective in the gelation of gelatin.

Figure 1C:
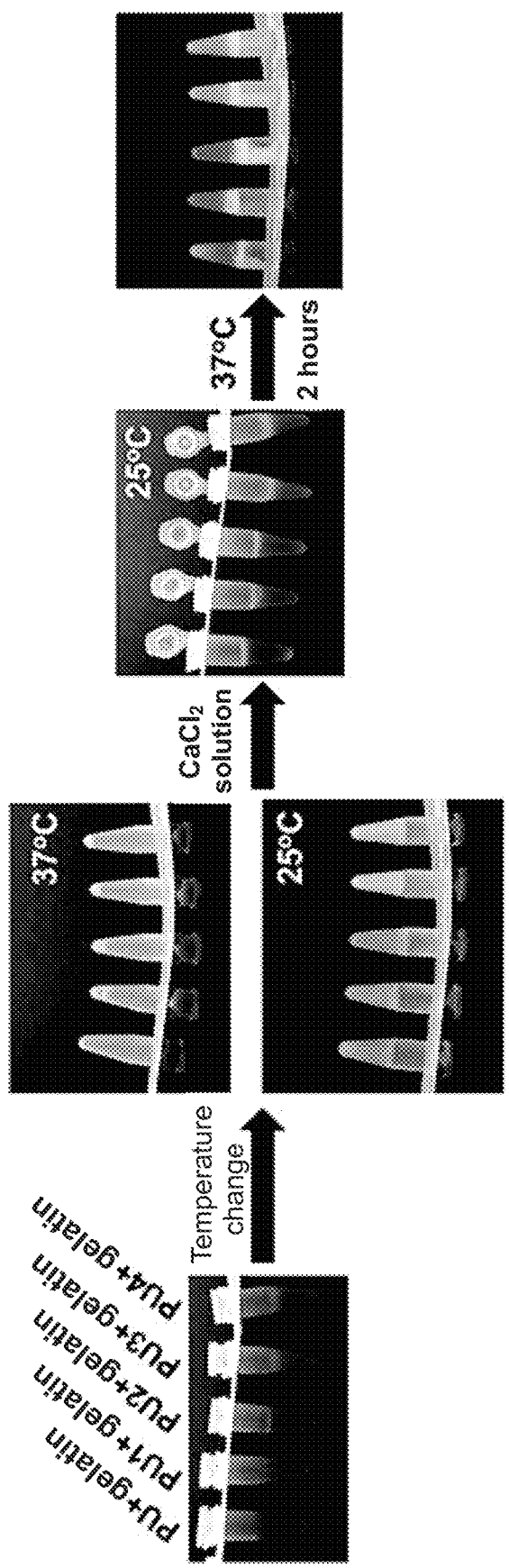
FIG. 1C shows the change in appearance at 25° C. and 37° C. after mixing a calcium chloride solution with various polyurethane/gelatin hydrogels.
Figure 1D:
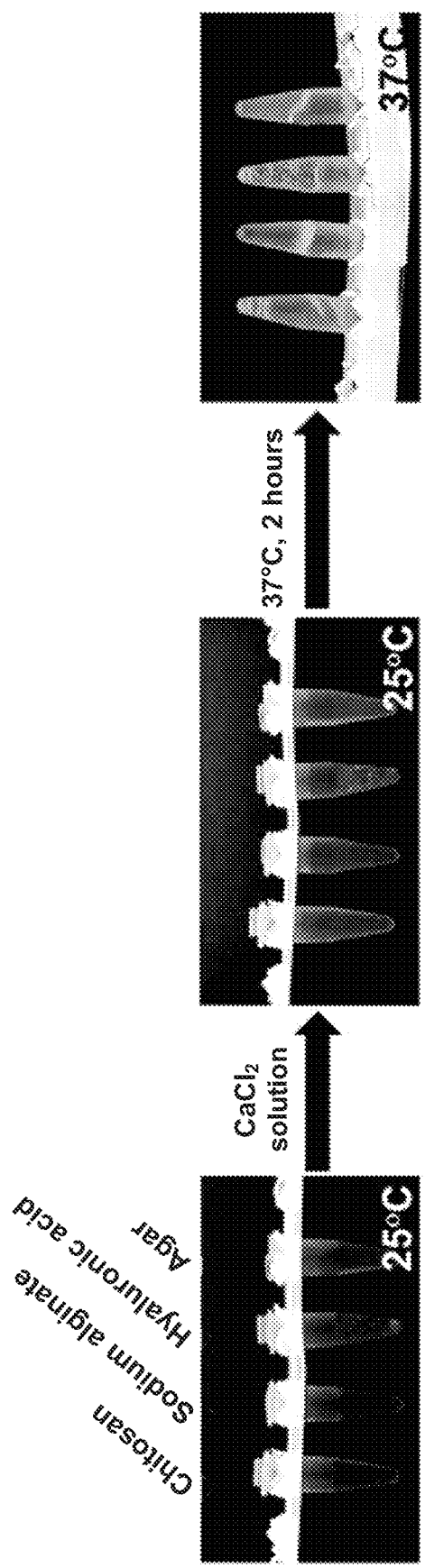
FIG. 1D shows the change in appearance at 25° C. and 37° C. after mixing a calcium chloride solution with an aqueous solution of chitosan, sodium alginate, hyaluronic acid, or agar.
Figure 1E:
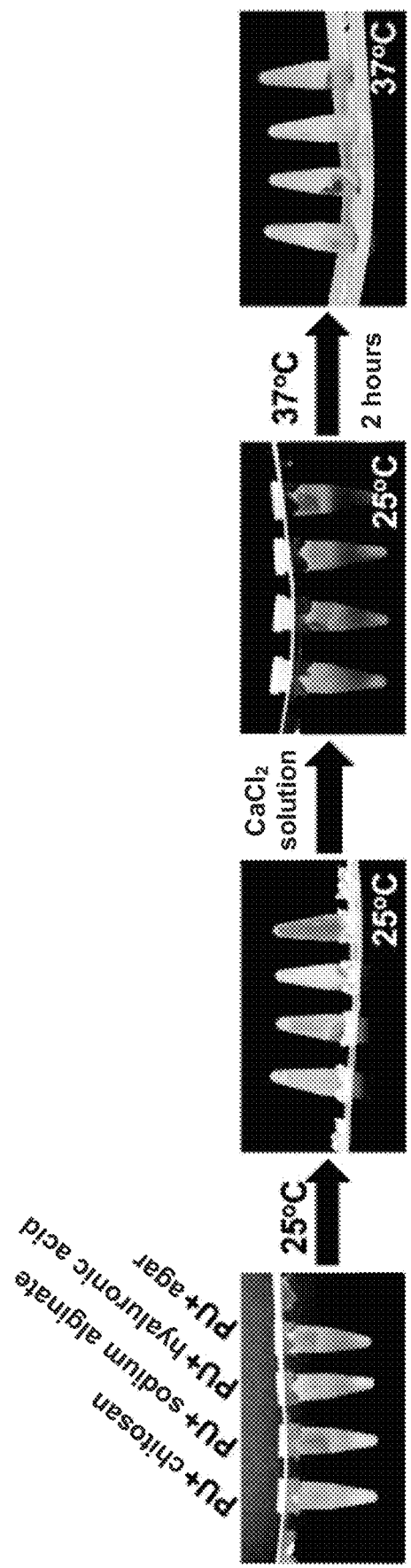
FIG. 1E shows the change in appearance at 25° C. and 37° C. after mixing a calcium chloride solution with the mixture of polyurethane (PU) dispersion and an aqueous solution of chitosan, sodium alginate, hyaluronic acid, or agar.

According to a procedure similar to that described above, a 0.2 N (0.1 M) calcium chloride solution was used to treat the following: the hydrogels prepared by mixing various biodegradable polyurethane dispersion (30 wt %) with a gelatin aqueous solution (10 wt %) at a solid content ratio of 80:20, the biopolymer aqueous solution of chitosan, sodium alginate, hyaluronic acid, or agar, and the mixtures of PU dispersion (30 wt %) and each of the aforementioned biopolymer aqueous solutions (5 wt %) at a solid content ratio of 80:20. The results are shown in FIGS. 1C-1E. According to FIG. 1C, the five different polyurethane/gelatin hydrogels, each of which contained different types of polyurethane (PU, PU1, PU2, PU3, and PU4), were all in gel form at 25° C., but they were liquid at 37° C. After treatment with the calcium ion solution, all of the polyurethane/gelatin hydrogels became gel-like at 37° C., indicating that treatment with divalent alkaline earth metal ions improves the gel formation ability of a variety of polyurethane/gelatin hydrogels. According to FIG. 1D, the aqueous solution of sodium alginate, hyaluronic acid, or agar was gel-like at 37° C. after treatment with the calcium ion solution, while the chitosan aqueous solution remained as liquid. According to FIG. 1E, the PU/chitosan mixture, PU/sodium alginate mixture, PU/hyaluronic acid mixture, and PU/agar mixture were gel-like at 37° C. after treated with the calcium ion solution, indicating that treatment with divalent alkaline earth metal ions promotes the gelation of various polyurethane/biopolymer mixtures.

2.2 Effects of Calcium Ion Treating Time on the Structural Stability of the Gel Object Formed from the Bioink The effect of calcium ion treating time on the overall structural stability of the gel object formed from the bioink was evaluated. First, a polyurethane/gelatin hydrogel containing DMEM-LG medium was printed as a gel object having a predetermined structure. The gel object was then immersed in a 0.2 N (0.1M) calcium chloride aqueous solution at 25° C. for 0, 5, 10, 15, 20, or 25 minutes, transferred to PBS, and incubated in a 37° C. incubator for 24 hours.

Figure 2A:
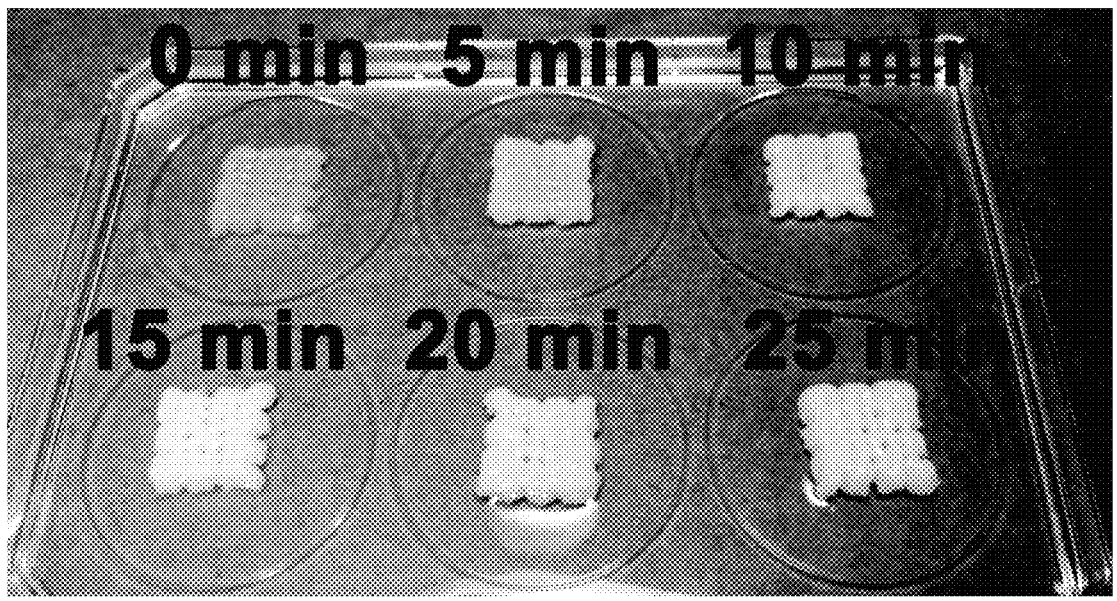
FIG. 2A shows the appearance of gel objects at various time points after immersing the gel objects in a calcium chloride solution at 25° C., wherein the gel objects were printed with a polyurethane/gelatin hydrogel containing DMEM-LG medium and having a predetermined structure.
Figure 2B:
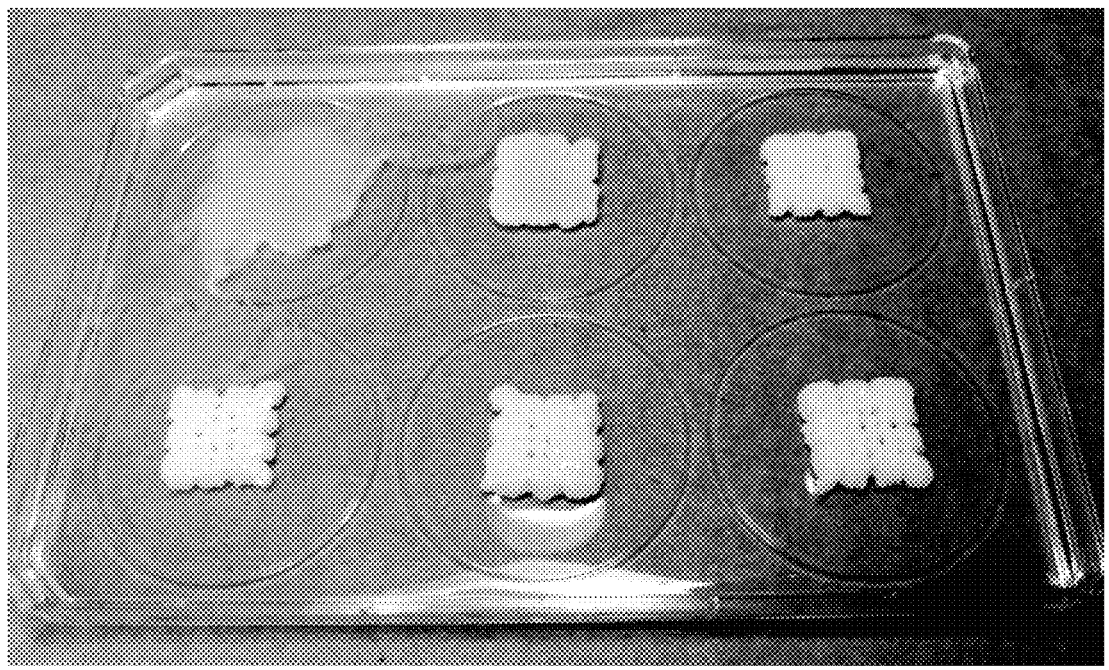
FIG. 2B shows the appearance of the gel objects shown in FIG. 2A after further incubation in PBS at 37° C. for 24 hours.
Figure 3A:
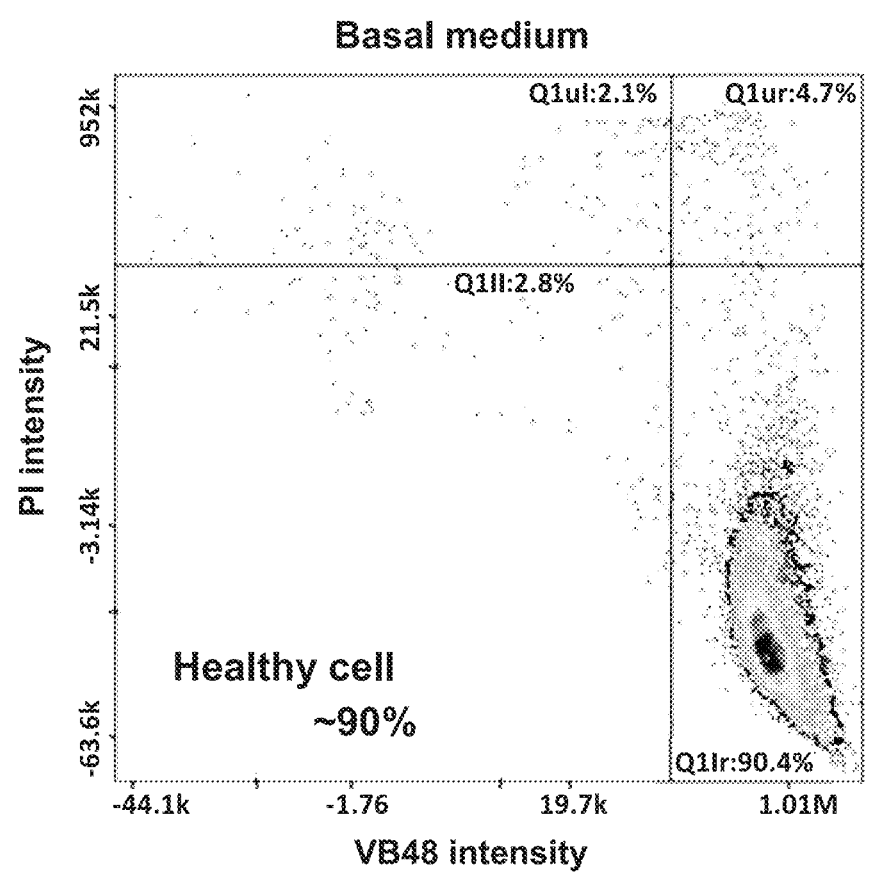
FIG. 3A shows the viability of human induced pluripotent stem cell-derived mesenchymal stem cells (referred to as hiPS-MSCs) in cell culture medium.
Figure 3B:
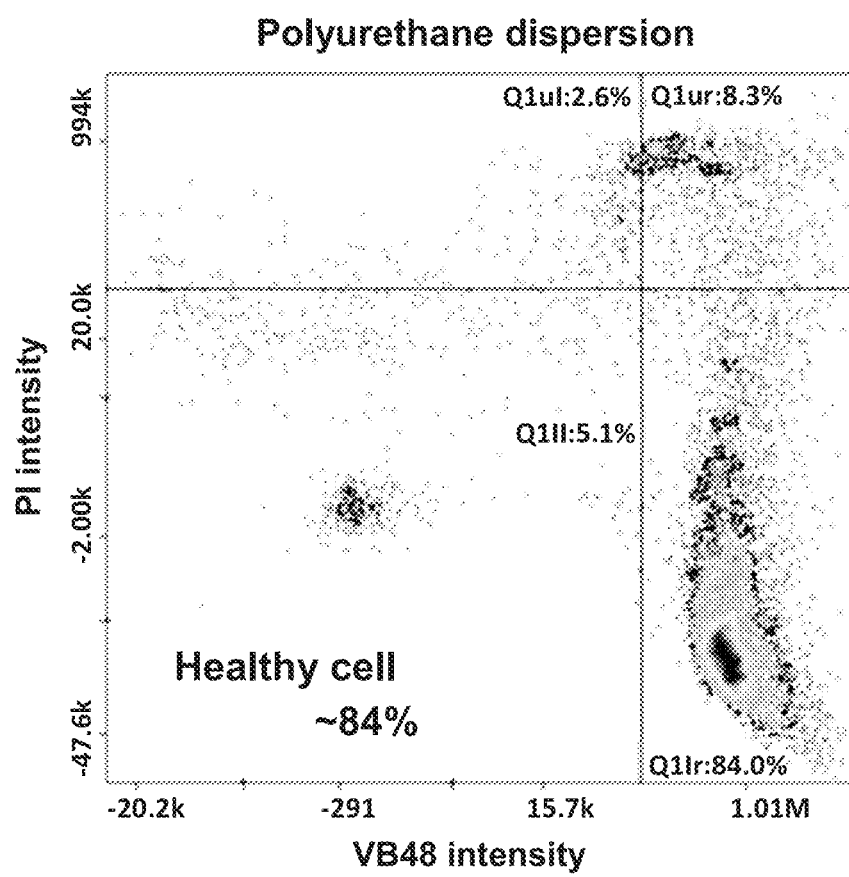
FIG. 3B shows the viability of hiPS-MSCs in polyurethane dispersion.
Figure 3C:
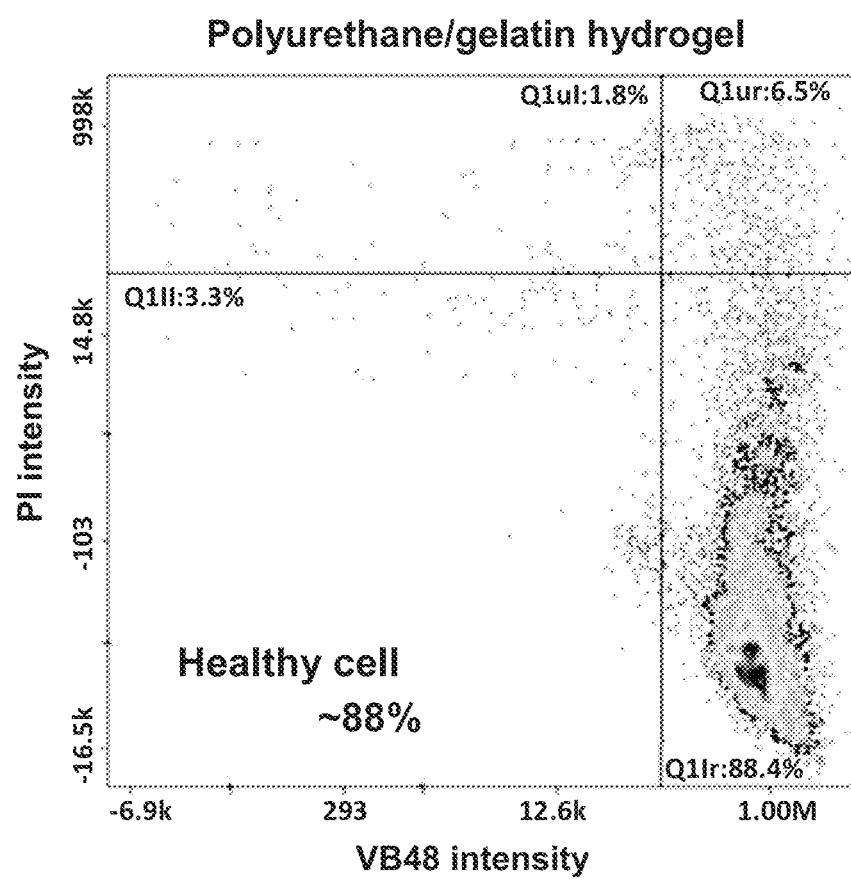
FIG. 3C shows the viability of hiPS-MSCs in polyurethane/gelatin hydrogel.
Figure 3D:
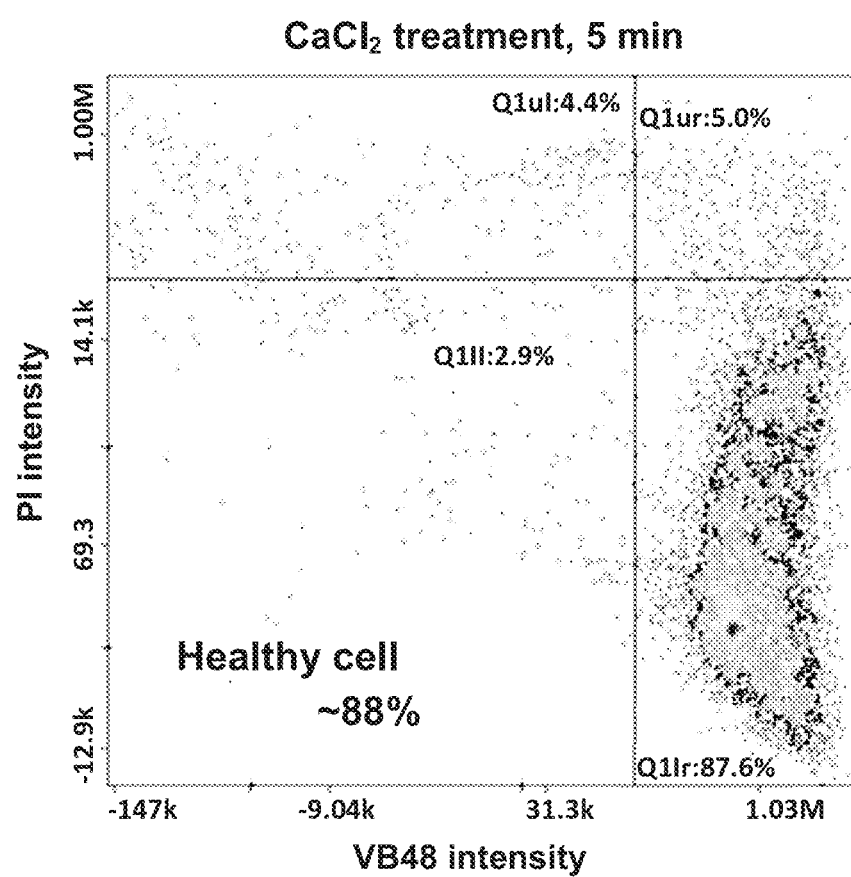
FIG. 3D shows the viability of hiPS-MSCs in polyurethane/gelatin hydrogel treated with calcium ions for 5 minutes.
Figure 3E:
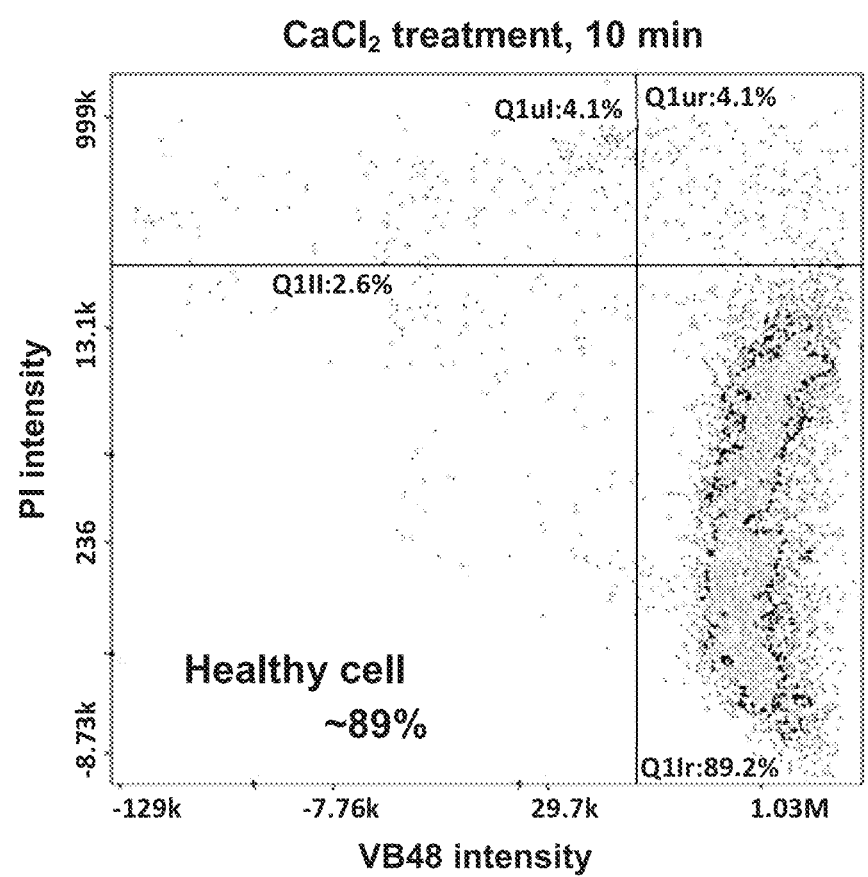
FIG. 3E shows the viability of hiPS-MSCs in polyurethane/gelatin hydrogel treated with calcium ions for 10 minutes.
Figure 3F:
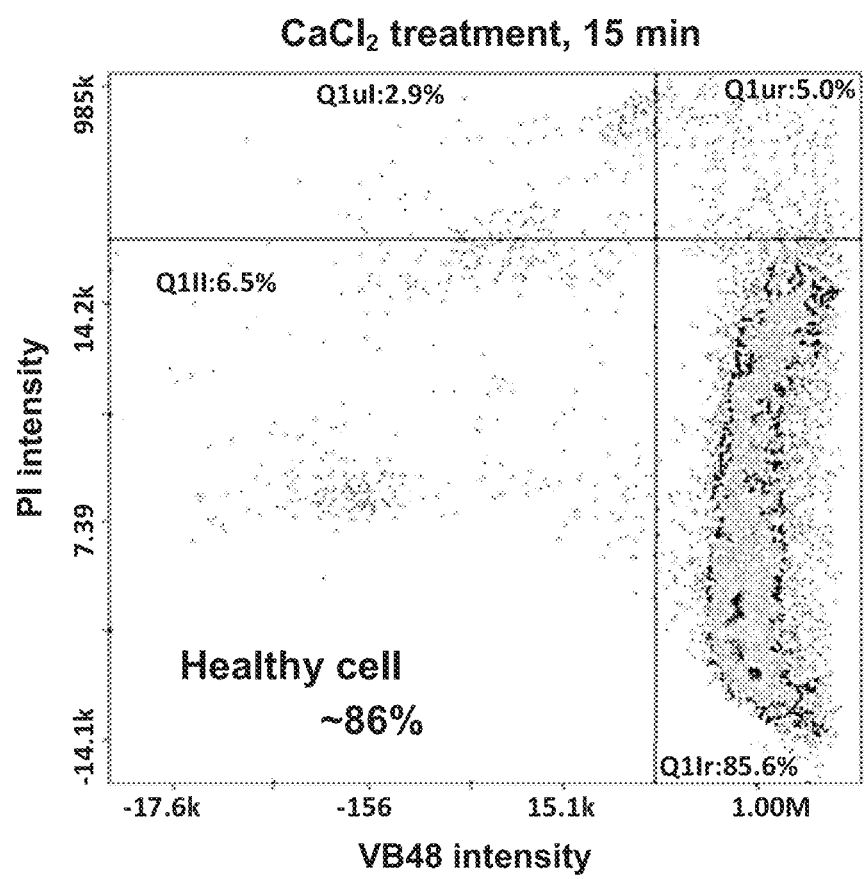
FIG. 3F shows the viability of hiPS-MSCs in polyurethane/gelatin hydrogel treated with calcium ions for 15 minutes.
Figure 3G:
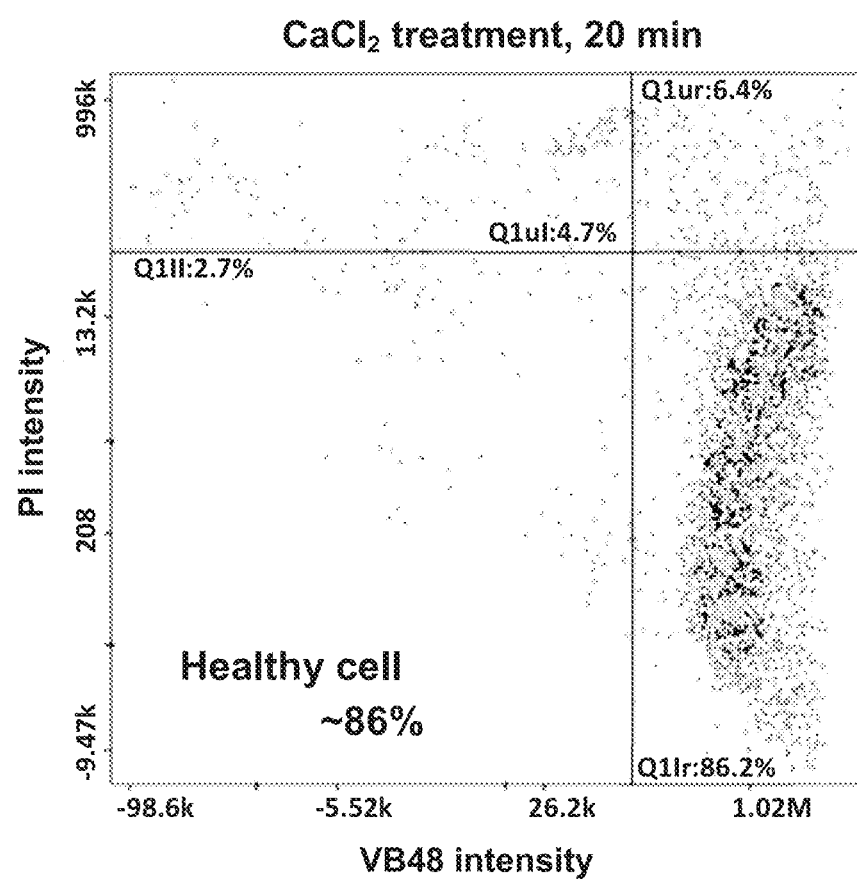
FIG. 3G shows the viability of hiPS-MSCs in polyurethane/gelatin hydrogel treated with calcium ions for 20 minutes.
Figure 3H:
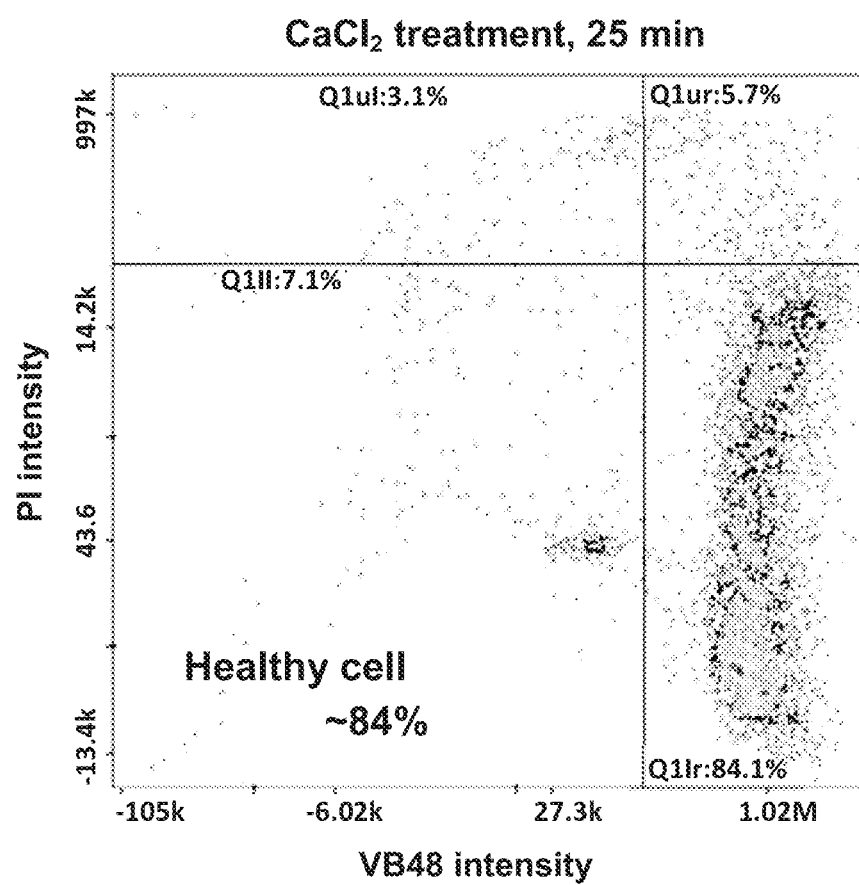
FIG. 3H shows the viability of hiPS-MSCs in polyurethane/gelatin hydrogel treated with calcium ions for 25 minutes.

FIG. 2A shows the appearance of the aforementioned gel objects that were immersed in a calcium chloride solution at 25° C. for various time periods; FIG. 2B shows the appearance of the gel objects treated with calcium chloride for a predetermined period of time and subsequently incubated in PBS at 37° C. for 24 hours. According to FIG. 2A, the structural stability of the gel objects increased with time when the calcium ion solution treating time was less than 15 minutes. However, the structural stability did not change significantly when the treating time exceeded 15 minutes. According to FIG. 2B, the gel objects that had been treated with the calcium ion solution for 15 minutes or more held the predetermined structure in PBS at 37° C. for at least 24 hours.

Example 3

Viability of hiPS-MSCs in the Bioink

In order to evaluate whether the treatment of bioink material and calcium ion affects cell survival, a comparison of viability was made for hiPS-MSC cells treated with the polyurethane dispersion or the polyurethane/gelatin hydrogel, or additionally treated with 0.2 N (0.1 M) calcium ion for different time periods. First, hiPS-MSC cells at a cell density of $3.6 \times 10^4$ cells/μL were added to the basal medium (control), the polyurethane dispersion, or the polyurethane/ gelatin hydrogel. Both the polyurethane dispersion and the polyurethane/gelatin hydrogel were supplemented with DMEM-LG medium and 3.7 g/L sodium bicarbonate. Also, another five groups of hiPS-MSC cells added to the polyurethane/gelatin hydrogel at $3.6 \times 10^4$ cells/4, were treated with a 0.2 N (0.1 M) calcium chloride aqueous solution for 5, 10, 15, 20, or 25 minutes. Each of the aforementioned cell groups was cultured at 25° C. for 1 hour (the treating time was included for the calcium ion-treated cells), and the cell viability was analyzed using a flow cytometer (Nucleocounter NC-3000). Prior to the analysis, propidium iodide (PI), acridine orange (AO), and the VB-48 fluorescent dye were used to stain the cells to indicate dead cells, total cells, and healthy cells, respectively.

FIGS. 3A-3H show the viability of hiPS-MSC cells. According to FIGS. 3A-3H, 90%, 84%, and 88% of total cells were found normal and healthy in the basal medium, polyurethane dispersion, and polyurethane/gelatin hydrogel without calcium chloride treatment, respectively. After treatment with calcium chloride for 5, 10, 15, 20, or 25 minutes, the proportions of the normal and healthy cells were approximately 88%, 89%, 86%, 86%, and 84%, respectively. The results show that cell activity gradually decreases as the calcium ion treating time increases. Therefore, the calcium ion treating time is preferably no more than 60 minutes.

Example 4

Rheological Properties of the Bioink

Figure 4A:
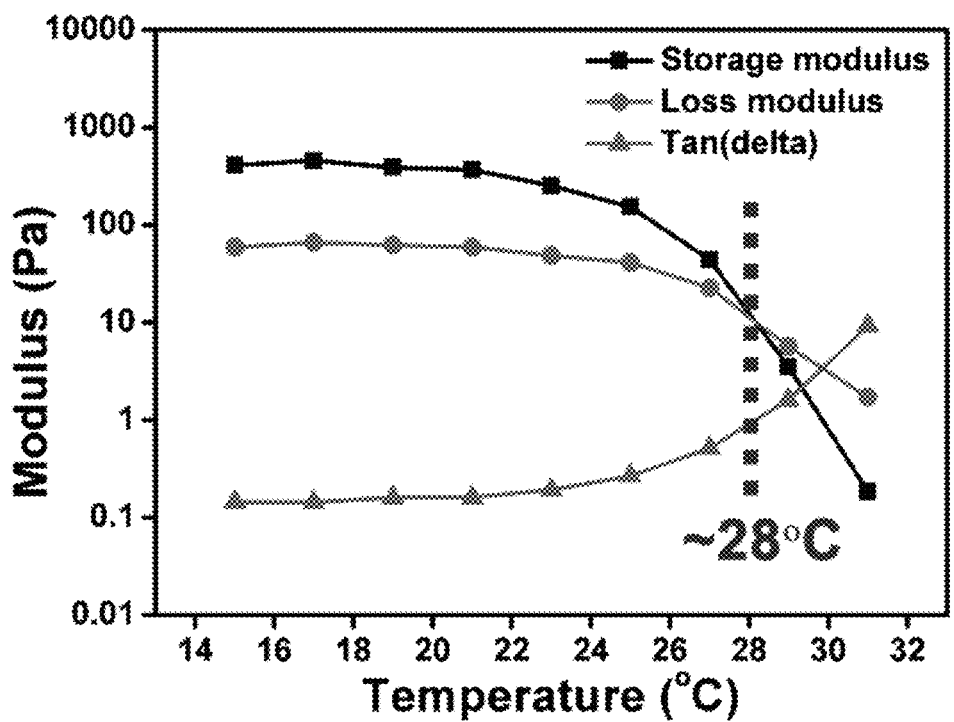
FIG. 4A shows oscillation temperature sweep of the polyurethane/gelatin hydrogel according to one embodiment of the present invention at a strain of 1% and a frequency of 1 Hz and the gelation temperature determined therefrom.
Figure 4B:
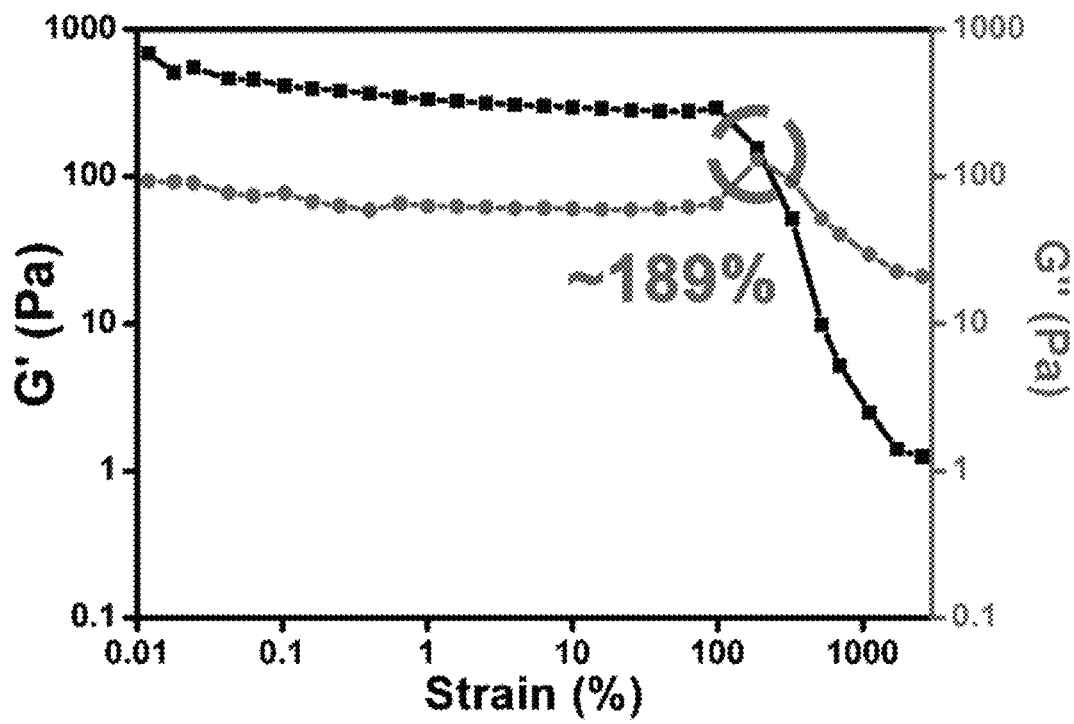
FIG. 4B shows a portion of oscillation strain sweep of the polyurethane/gelatin hydrogel according to one embodiment of the present invention at a strain range of 0.01-2500% and a frequency of 1 Hz at 25° C.

To evaluate the rheological properties of the bioink, rheological parameters of the polyurethane/gelatin hydrogel were measured using a cone rheometer, with the results shown in FIGS. 4A-4D. According to FIG. 4A, the gelation temperature of the polyurethane/gelatin hydrogel was about 28° C. FIG. 4B shows a portion of oscillation strain sweep of the polyurethane/gelatin hydrogel at a strain range of 0.01-2500% and a frequency of 1 Hz at 25° C., indicating that the polyurethane/gelatin hydrogel changed from gel state to liquid as the strain increased to 189%.

Figure 4C:
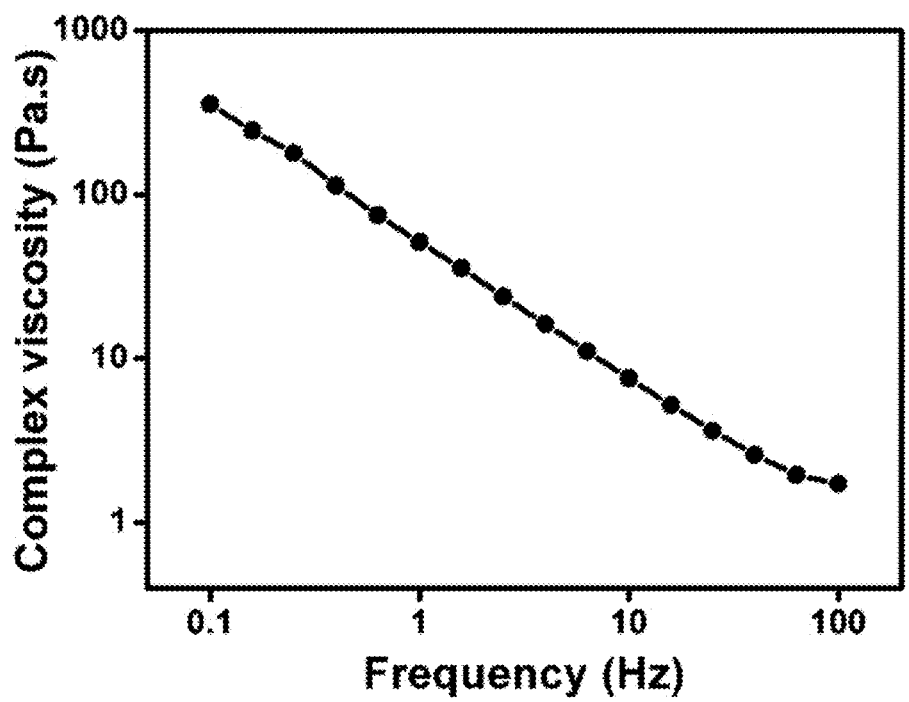
FIG. 4C shows the result of dynamic shear test on the polyurethane/gelatin hydrogel according to one embodiment of the present invention at a strain of 1% and a frequency range of 0.1-100 Hz at 25° C.
Figure 4D:
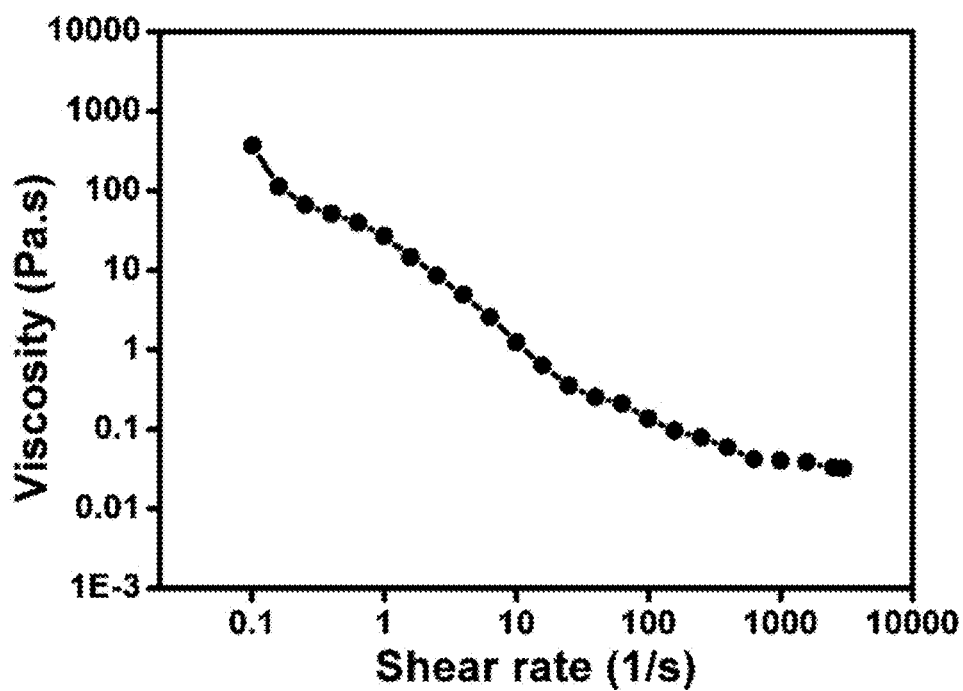
FIG. 4D shows the result of static shear test on the polyurethane/gelatin hydrogel according to one embodiment of the present invention at a shear rate range of 0.1-3000 $s^{-1}$.

FIG. 4C shows the result of dynamic shear test on the polyurethane/gelatin hydrogel at a strain of 1% and a frequency range of 0.1-100 Hz at 25° C.; FIG. 4D shows the result of static shear test on the polyurethane/gelatin hydrogel at a shear rate range of 0.1-3000 $s^{-1}$. According to FIG. 4C, the complex viscosity of the polyurethane/gelatin hydrogel decreased as the frequency increased, and the complex viscosity at 100 Hz was 1.7 Pa·s. According to FIG. 4D, shear thinning effect was observed in the polyurethane/ gelatin hydrogel, and the steady shear viscosity was 0.14 Pa·s at the shear rate of 100 $s^{-1}$.

Example 5

Printability of the Bioink

The bioink of the present invention can be utilized for 3D printing at room temperature. In one embodiment, by using a 3D printing apparatus connected to a computer where the information of a designed 3D pattern was stored and used as a blueprint, the bioink with proper viscoelasticity (such as the polyurethane/gelatin hydrogel described in Example 1) was printed through an extrusion process onto a platform that was maintained at 20-25° C. and deposited layer-by-layer to form a gel object having a predetermined structure. The gel object had sufficient mechanical strength to be clamped without destruction and moved to a divalent metal ion solution, such as a calcium chloride aqueous solution.

Figure 5:
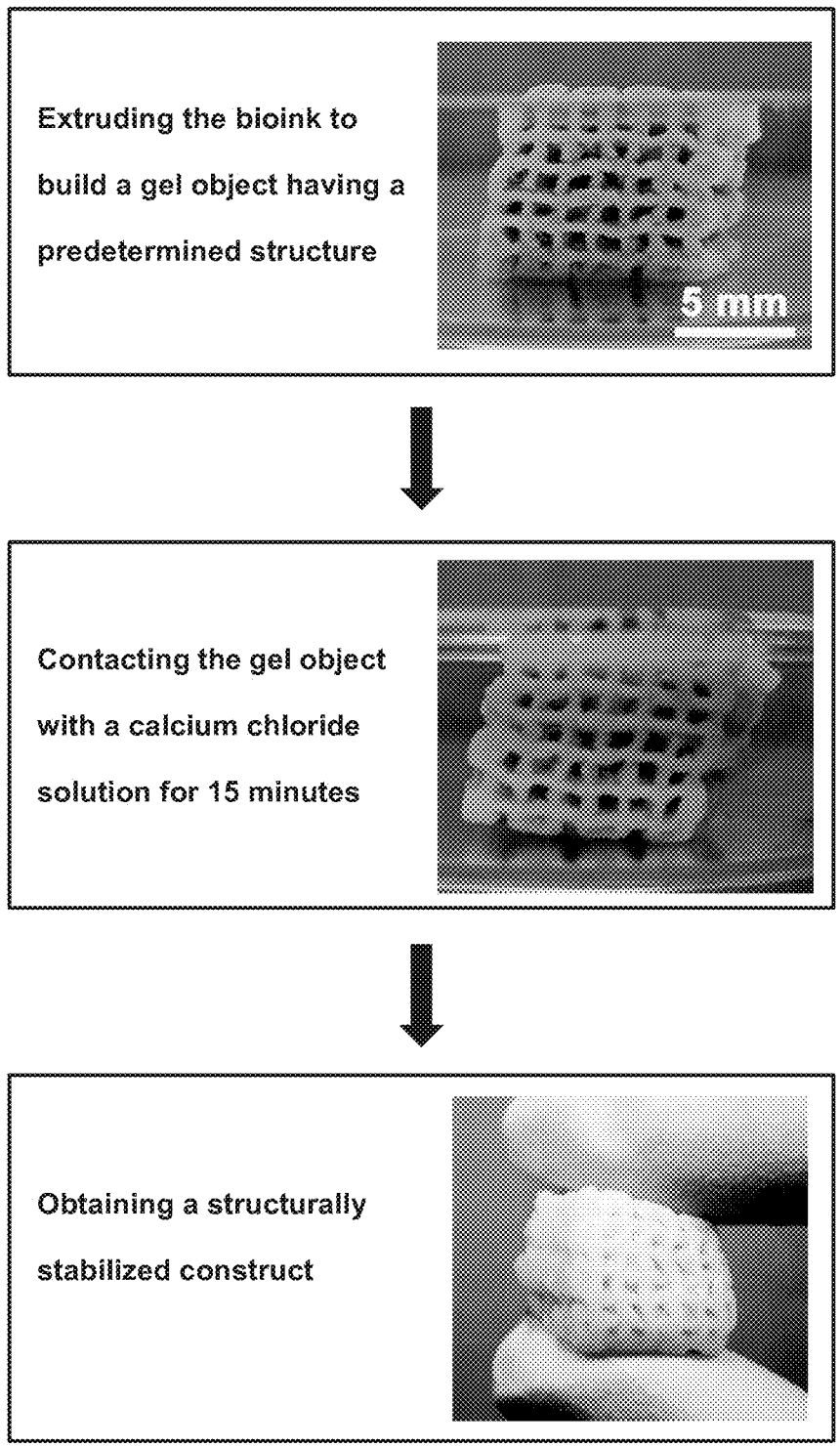
FIG. 5 shows an exemplary flow chart illustrating the method of the present invention for printing a construct that is able to carry cells, and shows photographs of a printed gel object having a grid structure and a structurally stabilized construct obtained by immersing the printed gel object in a calcium chloride solution for 15 minutes.

After the gel object contacted with the divalent metal ion at room temperature for a predetermined period of time (e.g., 15 minutes), a construct having that predetermined structure was obtained due to the increased structural stability. FIG. 5 shows an exemplary flow chart illustrating the abovementioned printing procedure along with the photographs of a printed gel object having a grid structure and a structurally stabilized construct obtained by immersing the printed gel object in the calcium chloride solution. In this case, the predetermined structure was maintained for at least 24 hours at a physiological temperature of 37° C.

Figure 6:
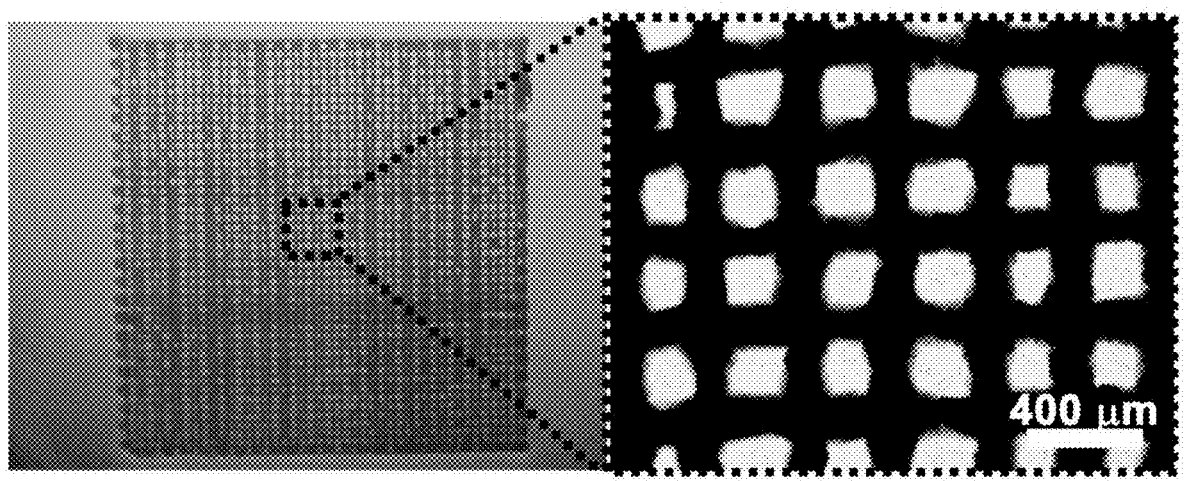
FIG. 6 shows a magnified image of a high-resolution gel object that was printed through a nozzle with a diameter of approximately 80 µm; an enlarged view of a portion of the image is shown on the right where the scale bar represents 400 µm.

The aforementioned 3D printing apparatus includes a syringe for extruding the bioink. The syringe includes a replaceable nozzle whose diameter is variable and determines the resolution and pattern fidelity of the printed product. As shown in FIG. 5, the gel object was printed through a nozzle having a diameter of approximately 200 µm. FIG. 6 shows a magnified image of a high-resolution gel object that was printed through a nozzle with a diameter of approximately 80 µm, where the hydrogel filament coming out of the nozzle had an average diameter of approximately 120±5 µm. Because of the rheological properties, the bioink of the present invention maintains proper viscoelasticity while the solid content of the polyurethane is reduced, and thus it can be utilized with nozzles having a diameter of at least 50 µm for high-resolution and high-fidelity 3D printing for more than 24 hours.

Example 6

Mechanical Properties of the Gel Formed from the Bioink

Figure 7A:
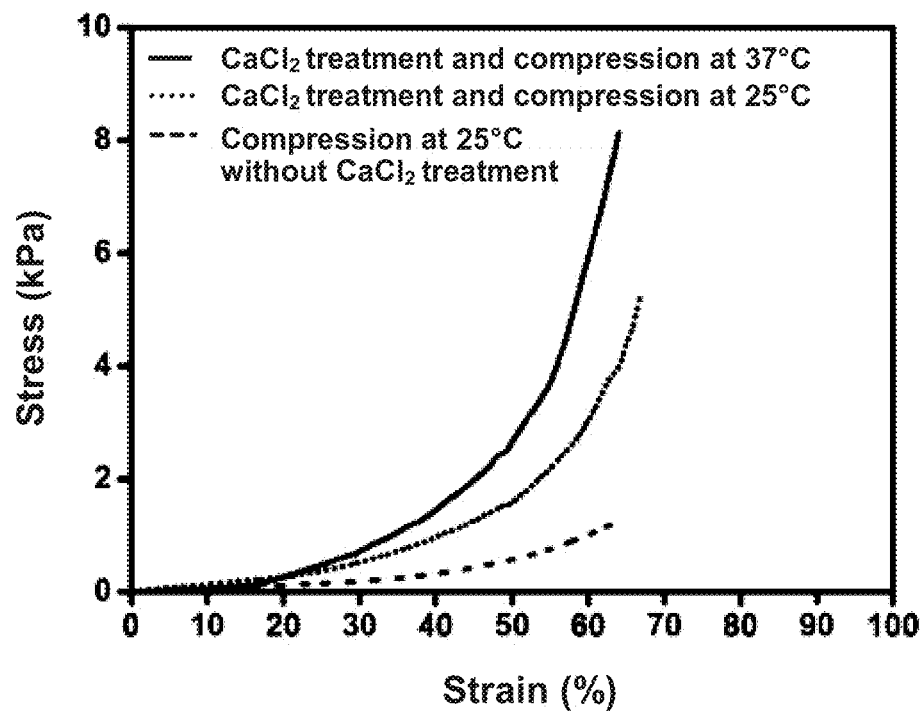
FIG. 7A shows the compressive properties of the polyurethane/gelatin hydrogel at 25° C. and 37° C. before and after treatment with a calcium chloride solution.
Figure 7B:
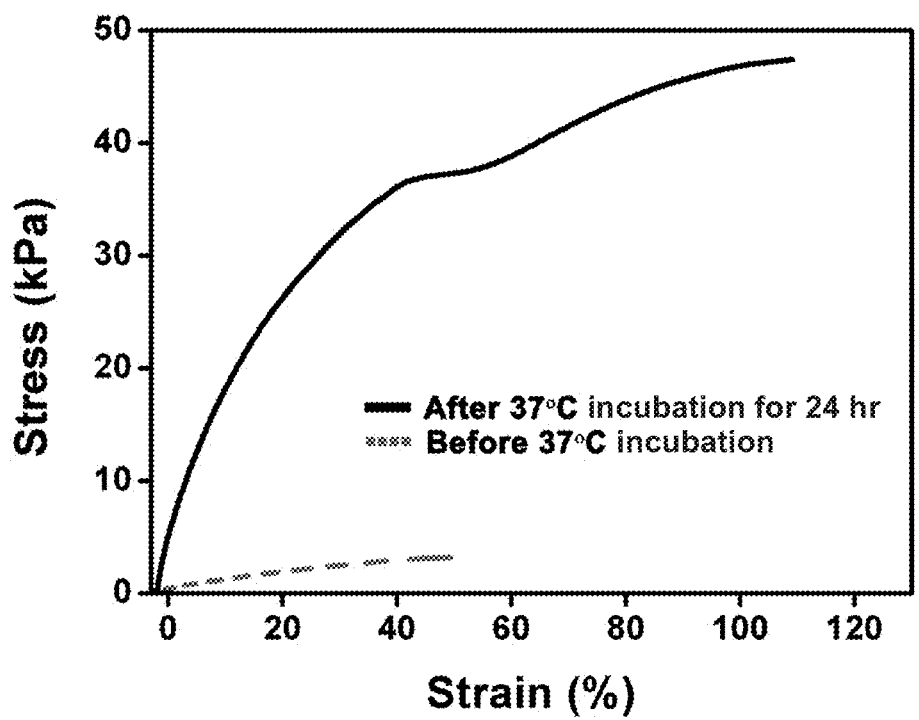
FIG. 7B shows the tensile properties of the polyurethane/gelatin hydrogel treated with a calcium chloride solution and optionally incubated at 37° C. for 24 hours.

To study the effect of divalent metal ion treatment on the mechanical properties of the gel formed from the bioink, the static compressive properties and tensile properties of the polyurethane/gelatin hydrogel, before and after treatment with a calcium chloride solution, were measured at 25° C. or 37° C. using a dynamic mechanical analyzer (DMA), with the results shown in FIGS. 7A-7B. According to FIG. 7A, treatment with the calcium chloride solution increased the maximum compressive strength and maximum deformation of the polyurethane/gelatin hydrogel at 25° C. from 1.2±0.1 kPa to 5.2±0.3 kPa and from 64±4.1% to 67±4.3%, respectively. Moreover, at 37° C., the maximum compressive strength and maximum deformation of the polyurethane/gelatin hydrogel treated with calcium chloride solution were 8.1±0.5 kPa and 64±3.9%, respectively, whereas the mechanical properties prior to calcium chloride solution treatment were not available because the polyurethane/gelatin hydrogel without such treatment was unable to maintain a specific structure at 37° C. According to FIG. 7B, after treatment with the calcium chloride solution and incubation at 37° C. for 24 hours, the polyurethane/gelatin hydrogel had enhanced mechanical properties, with the Young's modulus slightly increasing from 0.1±0.0 to 1.3±0.1 kPa, the maximum tensile strength increasing from 3.4±0.2 kPa to 47±2.8 kPa, and the elongation at break increasing from 90±5.5% to 109±8.8%.

Example 7

Physiological Behavior of hiPS-MSCs in the Bioink
7.1 Cell Proliferation

This example illustrates the long-term effects on cell growth and differentiation of the construct printed with the bioink. First, the hiPS-MSCs were treated with or without a cell membrane labeling fluorescent dye PKH26 (with an excitation wavelength of 551 nm and an emission wavelength of 567 nm). To prepare the cell-included bioink, the two cell groups were separately added at a cell density of $6 \times 10^6$ cells/mL to the polyurethane/gelatin hydrogel supplemented with DMEM-LG medium and 3.7 g/L sodium bicarbonate. Thereafter, a syringe of a 3D printing apparatus was filled with the bioink containing the hiPS-MSCs, and 3D printing was performed under the following conditions: the temperature of printing platform was 20-25° C., the nozzle diameter was 80 µm, and the nozzle temperature was 20-35° C., preferably 24-31° C., with air pressure of 50-300 kPa. After printing, the cell-laden gel object having a predetermined structure was soaked in a 0.2 N (0.1 M) calcium chloride aqueous solution for 15 minutes to form a cell-laden construct, and then the construct was transferred to a 37° C. incubator and incubated in the basal medium for ten days. The PKH26-labeled cells were monitored continuously for their growth in the construct using a real-time camera system (CCM-MULTI; Astec, Japan). To quantify cell proliferation, the construct carrying the unlabeled cells were treated with 2-(2-methoxy-4-nitrophenyl)-3-(4-nitrophenyl)-5-(2,4-disulfophenyl)-2H-tetrazolium monosodium salt (WST-8; purchased from Sigma) and the absorbance at 460 nm was measured using a spectrometer (SpectraMax M5; Molecular Devices, USA).

Figure 8:
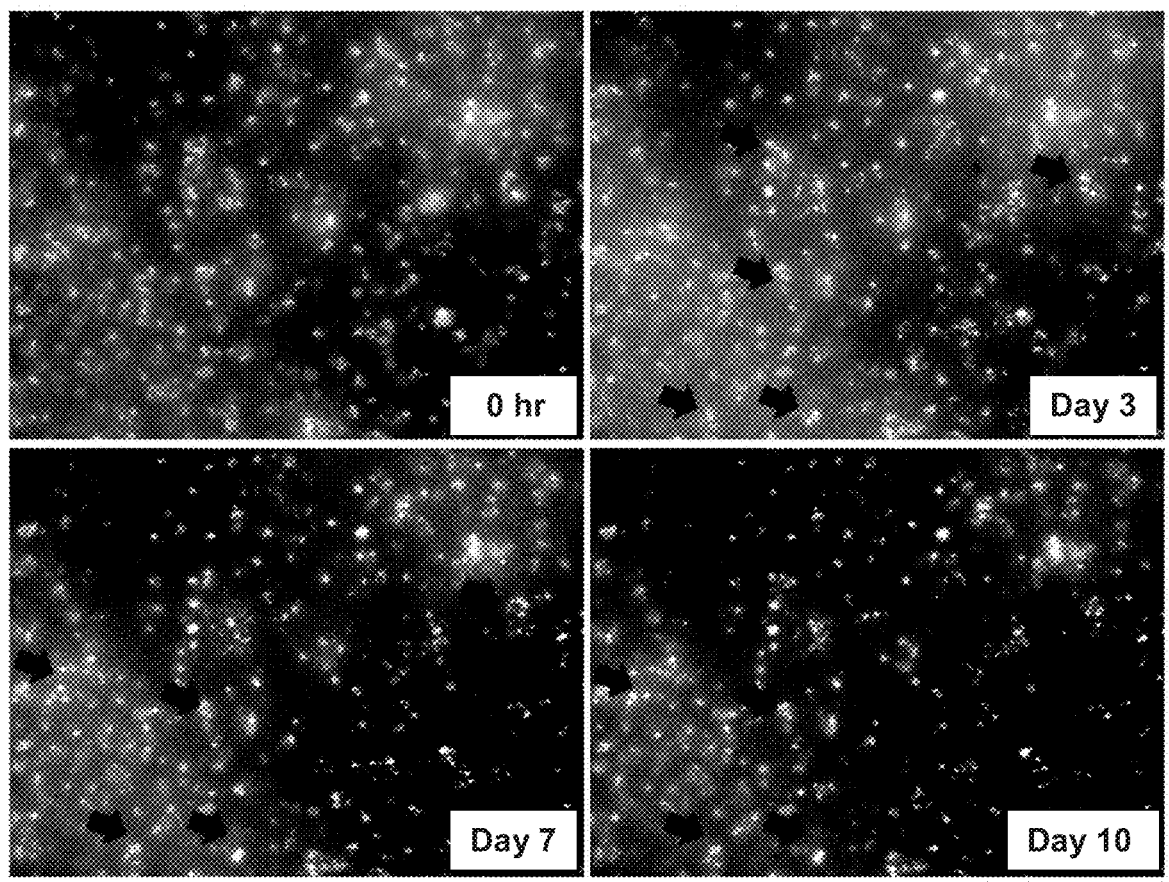
FIG. 8 shows the fluorescence images of PKH26-stained hiPS-MSCs during ten days of incubation in a construct of polyurethane/gelatin hydrogel; the arrows indicate significant cell migration or proliferation.
Figure 9:
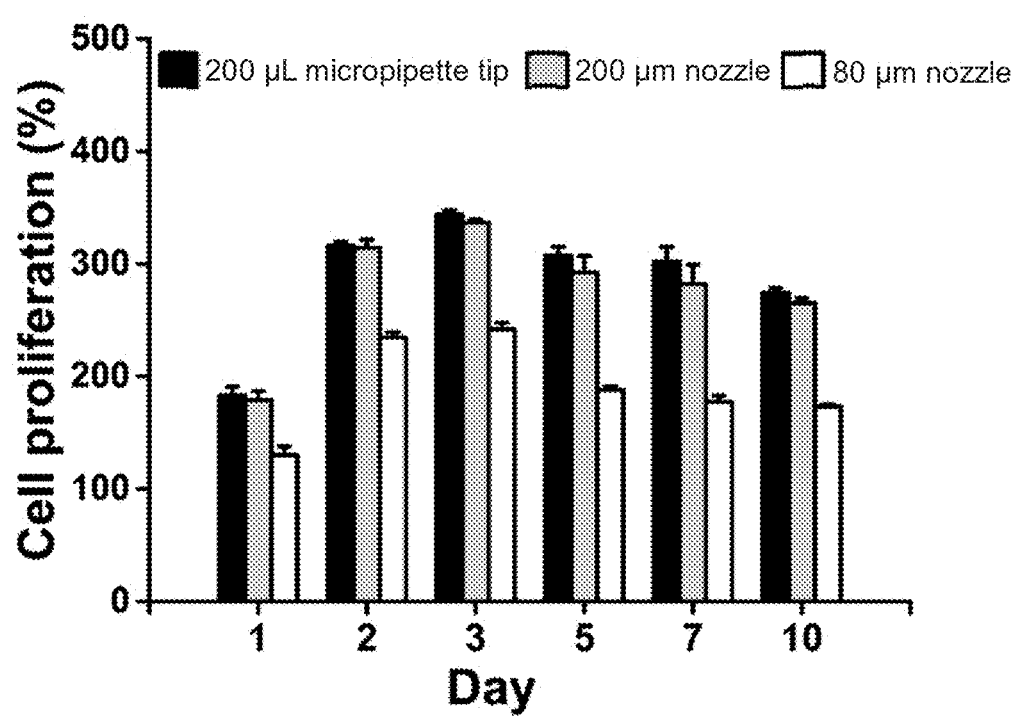
FIG. 9 shows the percent proliferation of hiPS-MSCs during ten days of incubation in a construct of polyurethane/gelatin hydrogel.
Figure 10A:
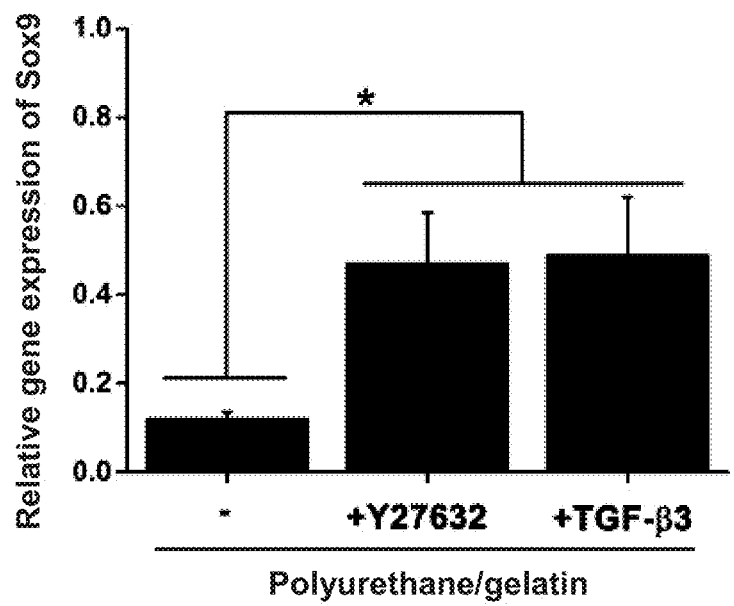
FIGS. 10A-10E show the relative gene expression levels of sex determining region Y-box 9 (Sox9), aggrecan (Agg), type II collagen (Col II), type I collagen (Col I), and type X collagen (Col X), respectively, in the hiPS-MSCs subjected to seven days of chondrogenic induction in a construct of polyurethane/gelatin hydrogel, where * indicates $p<0.05$.
Figure 10B:
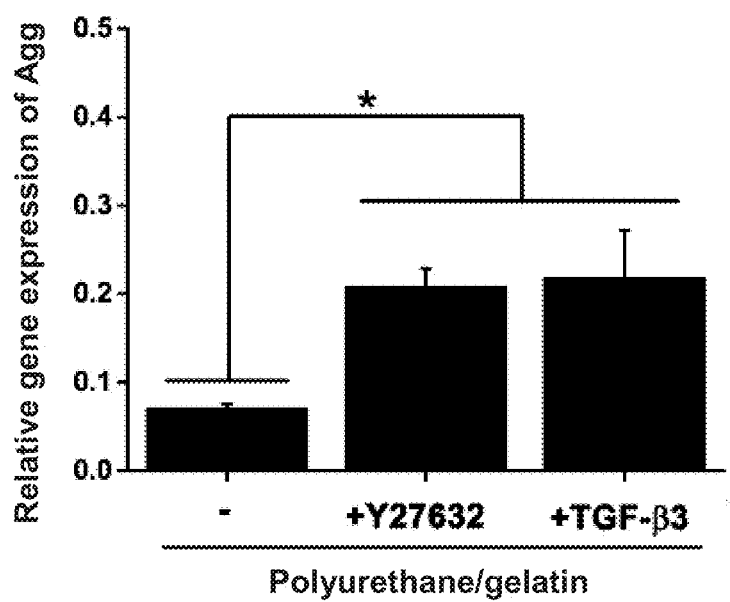
Figure 10C:
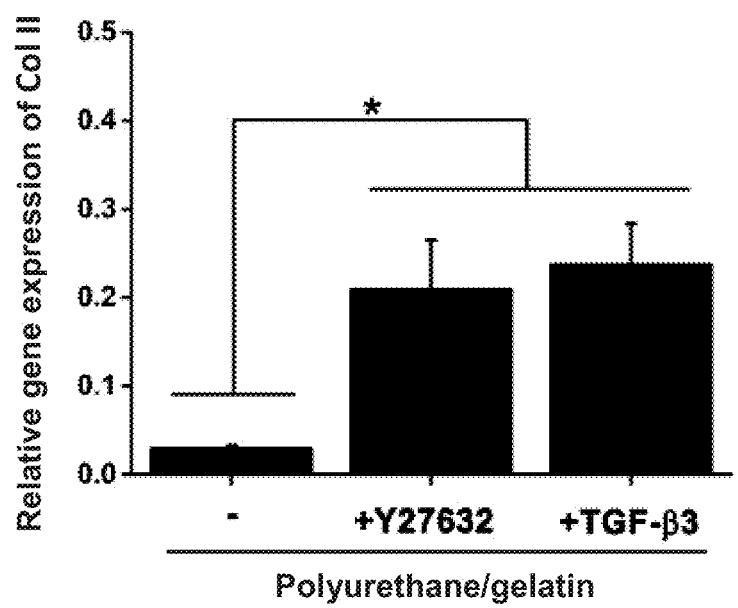
Figure 10D:
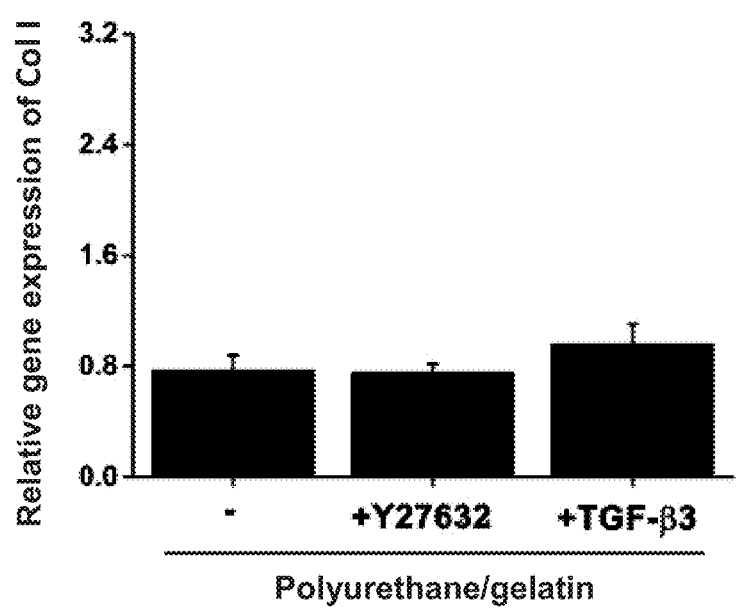
Figure 10E:
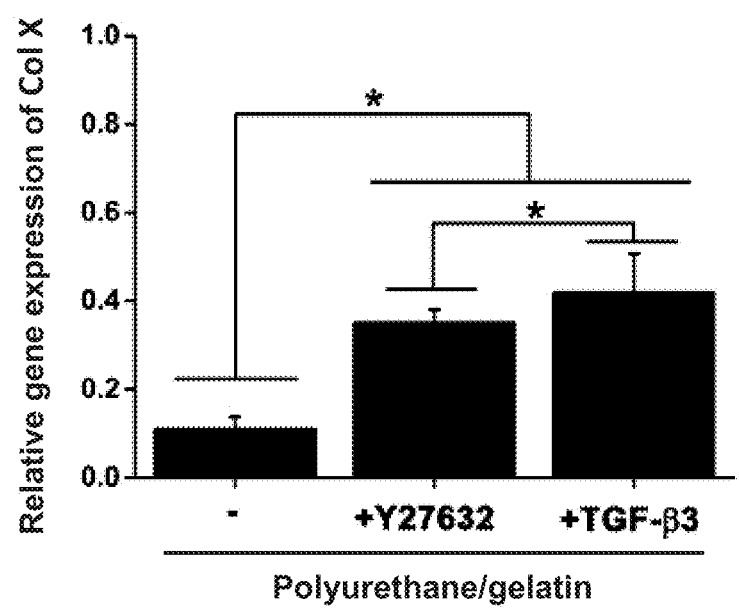

FIG. 8 shows the fluorescence images of PKH26-labelled hiPS-MSCs during ten days of incubation; FIG. 9 shows the percent proliferation of hiPS-MSCs in the construct during ten days of incubation. The percent proliferation is defined as the ratio of absorbance after incubation of cells for the indicated days and absorbance at 0 hour of incubation. According to FIG. 8, the hiPS-MSCs remained actively alive for at least ten days in the construct formed from the polyurethane/gelatin hydrogel. According to FIG. 9, 3D printing with a nozzle having a diameter of 200 µm did not significantly interfere with the growth and viability of cells in the construct compared to those of hiPS-MSCs printed with a 200 µL micropipette tip. Comparatively, printing with a nozzle having a diameter of 80 µm did affect cell growth and viability, because the cells endured larger shear stress as they passed through the nozzle.

7.2 Cell Differentiation

A construct carrying hiPS-MSCs and containing Y27632, a cell differentiation inducer, and TGF-β3, a chondrogenic inducer, was prepared according to a procedure similar to that described in Example 7.1. The construct was incubated in the basal medium for 24 hours and then incubated with a chondrogenic induction medium for seven days, followed by determination of chondrogenic gene expression in the cells using qPCR technique.

FIGS. 10A-10E show the relative gene expression levels of Sox9, Agg, Col II, Col I, and Col X in the hiPS-MSCs subjected to seven days of chondrogenic induction in the aforementioned construct. According to FIGS. 10A-10E, Y27632 or TGF-β3 had similar chondrogenic effects on the hiPS-MSCs in the polyurethane/gelatin hydrogel, including upregulation of the expression of chondrogenic genes such as Sox9, Agg, and Col II, and the gene of Col X which promotes chondrocyte hypertrophy. The enhancement of Col X gene expression by TGF-β3 was more significant than that by Y27632. In contrast, the gene expression of Col I, which is associated with chondrocyte fibrosis, showed no significant difference among groups. The results indicate that the mesenchymal stem cells are capable of maintaining stemness and differentiation potency in the construct formed from the bioink of the present invention.

In conclusion, the bioink material of the present invention has high biocompatibility and specific rheological properties and thus is suitable for high-resolution, high-fidelity, and long-term 3D bioprinting. Moreover, the printing method of the present invention effectively enhances the mechanical properties and structural stability of printed products by the interactions between polyurethanes, biopolymers, and divalent metal ions without impairing cell viability. Therefore, the bioink and printing method of the present invention can be used to produce artificial tissues or scaffolds for living organisms, or to produce in vitro drug screening platforms.

In addition, by adjusting the composition of the bioink, for example, the constituents of the main chain of the biodegradable polyurethane or the type of biopolymer, the present invention can be utilized to prepare printed products with different degradation rates and mechanical properties.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A bioink set, comprising:
    a bioink;
    a divalent metal ion solution; and
    a syringe including a nozzle having a diameter no more than 80 μm;
    wherein the bioink comprises a biodegradable polyurethane and a biopolymer selected from the group consisting of gelatin, agar, chitosan, and any combinations thereof;
    wherein the biodegradable polyurethane and the biopolymer are mixed to form a polyurethane/biopolymer hydrogel, the polyurethane/biopolymer hydrogel has a complex viscosity of 1.7 Pa·s at a frequency of 100 Hz, and the polyurethane/biopolymer hydrogel has a steady shear viscosity of 0.14 Pa·s at a shear rate of 100 $s^{-1}$;
    wherein the polyurethane/biopolymer hydrogel is treated with the divalent metal ion solution at 37° C., for enhancing a maximum compressive strength to 7.6-8.6 kPa, a maximum deformation to 60.1-67.9%, Young's modulus increasing from 0.1 to 1.4 kPa, maximum tensile strength increasing from 3.2 kPa to 49.8 kPa, and elongation at break increasing from 84.5% to 117.8%;
    wherein the biodegradable polyurethane and the biopolymer are at a weight ratio ranging from 85:15 to 5:95;
    wherein the biodegradable polyurethane comprises a hard segment conjugated to a soft segment, the hard segment is formed by reacting diisocyanate with a chain extender, the soft segment is at least an oligomer diol, and the chain extender comprises an anionic chain extender; and
    wherein the bioink is extruded through the syringe.

2. The bioink set of claim 1, wherein the divalent metal ion solution comprises a divalent alkaline earth metal ion.

3. The bioink set of claim 1, wherein the anionic chain extender is 2,2-bis(hydroxymethyl)propionic acid (DMPA).

4. The bioink set of claim 1, wherein the bioink has a solid content ranging from 12.5-21.4% (w/w).

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<223> OTHER INFORMATION: PCR primer

<400> SEQUENCE: 1
ttgagcctta aaacggtgct                                         20

<210> SEQ ID NO 2
<211> LENGTH: 20
<212> TYPE: DNA
<213> ORGANISM: Artificial sequence
<220> FEATURE:
<223> OTHER INFORMATION: PCR primer

<400> SEQUENCE: 2
ctggtgttct gagaggcaca                                         20

<210> SEQ ID NO 3
<211> LENGTH: 20
<212> TYPE: DNA
<213> ORGANISM: Artificial sequence
<220> FEATURE:
<223> OTHER INFORMATION: PCR primer

<400> SEQUENCE: 3
acagctgggg acattagtgg                                         20

<210> SEQ ID NO 4
<211> LENGTH: 20
<212> TYPE: DNA
<213> ORGANISM: Artificial sequence
<220> FEATURE:
<223> OTHER INFORMATION: PCR primer

<400> SEQUENCE: 4
gtggaatgca gaggtggttt                                         20

<210> SEQ ID NO 5
<211> LENGTH: 25
<212> TYPE: DNA
<213> ORGANISM: Artificial sequence
<220> FEATURE:
<223> OTHER INFORMATION: PCR primer

<400> SEQUENCE: 5
gaagagtgga gagtactgga ttgac                                   25

<210> SEQ ID NO 6
<211> LENGTH: 23
<212> TYPE: DNA
<213> ORGANISM: Artificial sequence
```

-continued

```
<220> FEATURE:
<223> OTHER INFORMATION: PCR primer

<400> SEQUENCE: 6
ggttcttgct gatgtaccag ttc                                      23

<210> SEQ ID NO 7
<211> LENGTH: 20
<212> TYPE: DNA
<213> ORGANISM: Artificial sequence
<220> FEATURE:
<223> OTHER INFORMATION: PCR primer

<400> SEQUENCE: 7
tcacgtacac tgccctgaag                                          20

<210> SEQ ID NO 8
<211> LENGTH: 20
<212> TYPE: DNA
<213> ORGANISM: Artificial sequence
<220> FEATURE:
<223> OTHER INFORMATION: PCR primer

<400> SEQUENCE: 8
tgcaacggat tgtgttgttt                                          20

<210> SEQ ID NO 9
<211> LENGTH: 20
<212> TYPE: DNA
<213> ORGANISM: Artificial sequence
<220> FEATURE:
<223> OTHER INFORMATION: PCR primer

<400> SEQUENCE: 9
tcaccaaaga agtcctgcta                                          20

<210> SEQ ID NO 10
<211> LENGTH: 22
<212> TYPE: DNA
<213> ORGANISM: Artificial sequence
<220> FEATURE:
<223> OTHER INFORMATION: PCR primer

<400> SEQUENCE: 10
gatacctcct ggatgtttcc ta                                       22

<210> SEQ ID NO 11
<211> LENGTH: 20
<212> TYPE: DNA
<213> ORGANISM: Artificial sequence
<220> FEATURE:
<223> OTHER INFORMATION: PCR primer

<400> SEQUENCE: 11
tcactgccac ccagaagact                                          20

<210> SEQ ID NO 12
<211> LENGTH: 20
<212> TYPE: DNA
<213> ORGANISM: Artificial sequence
<220> FEATURE:
<223> OTHER INFORMATION: PCR primer

<400> SEQUENCE: 12
ttctagacgg caggtcaggt                                          20
```